United States Patent
Zhang et al.

(10) Patent No.: US 12,049,495 B2
(45) Date of Patent: *Jul. 30, 2024

(54) STABLE PROTEIN SOLUTION FORMULATION CONTAINING HIGH CONCENTRATION OF AN ANTI-VEGF ANTIBODY

(71) Applicant: Novartis AG, Basel (CH)

(72) Inventors: Huixiang Zhang, Fort Worth, TX (US); Charles Boring, Fort Worth, TX (US); Alok Kulshreshtha, Grapevine, TX (US); Yuhong Zeng, Fort Worth, TX (US); Li Wan, Fort Worth, TX (US); Laman Alani, Fort Worth, TX (US)

(73) Assignee: NOVARTIS AG, Basel (CH)

( * ) Notice: Subject to any disclaimer, the term of this patent is extended or adjusted under 35 U.S.C. 154(b) by 556 days.

This patent is subject to a terminal disclaimer.

(21) Appl. No.: 16/871,765

(22) Filed: May 11, 2020

(65) Prior Publication Data

US 2020/0270336 A1 Aug. 27, 2020

Related U.S. Application Data

(62) Division of application No. 14/934,666, filed on Nov. 6, 2015, now Pat. No. 10,689,438.

(60) Provisional application No. 62/088,061, filed on Dec. 5, 2014, provisional application No. 62/076,770, filed on Nov. 7, 2014.

(51) Int. Cl.
*A61K 39/395* (2006.01)
*A61B 3/12* (2006.01)
*A61B 5/00* (2006.01)
*A61K 9/00* (2006.01)
*A61K 9/08* (2006.01)
*A61K 9/19* (2006.01)
*C07K 16/22* (2006.01)
*A61K 39/00* (2006.01)

(52) U.S. Cl.
CPC ............ *C07K 16/22* (2013.01); *A61B 3/12* (2013.01); *A61B 5/4848* (2013.01); *A61K 9/0048* (2013.01); *A61K 39/3955* (2013.01); *A61K 39/39591* (2013.01); *A61K 2039/54* (2013.01); *A61K 2039/545* (2013.01); *C07K 2317/24* (2013.01); *C07K 2317/52* (2013.01); *C07K 2317/522* (2013.01); *C07K 2317/56* (2013.01); *C07K 2317/565* (2013.01); *C07K 2317/567* (2013.01); *C07K 2317/569* (2013.01); *C07K 2317/622* (2013.01); *C07K 2317/76* (2013.01); *C07K 2317/94* (2013.01)

(58) Field of Classification Search
CPC ............................ A61K 39/395; C07K 16/22
See application file for complete search history.

(56) References Cited

U.S. PATENT DOCUMENTS

| 6,267,958 B1 * | 7/2001 | Andya ............... A61K 38/16 424/155.1 |
|---|---|---|
| 8,293,235 B2 | 10/2012 | Borras et al. |
| 8,349,322 B2 | 1/2013 | Borras et al. |
| 8,673,310 B2 | 3/2014 | Borras et al. |
| 8,937,162 B2 | 1/2015 | Borras et al. |
| 9,090,684 B2 | 7/2015 | Borras et al. |
| 9,422,366 B2 | 8/2016 | Borras et al. |
| 9,593,161 B2 | 3/2017 | Borras et al. |
| 9,873,737 B2 | 1/2018 | Borras et al. |
| 10,035,850 B2 | 7/2018 | Gekkieva et al. |
| 10,087,244 B2 | 10/2018 | Borras et al. |
| 10,100,111 B2 | 10/2018 | Borras et al. |
| 10,590,193 B2 | 3/2020 | Borras et al. |
| 10,689,438 B2 | 6/2020 | Zhang et al. |
| 11,098,110 B2 | 8/2021 | Gekkieva et al. |
| 2006/0088523 A1 | 4/2006 | Andya et al. |
| 2007/0071675 A1 | 3/2007 | Wu et al. |
| 2011/0226650 A1 | 9/2011 | Gokarn et al. |
| 2013/0004484 A1 | 1/2013 | Demeule et al. |
| 2014/0004131 A1 | 1/2014 | Mueller et al. |
| 2014/0186373 A1 | 7/2014 | Cosenza et al. |
| 2018/0127493 A1 | 5/2018 | Borras et al. |
| 2018/0371074 A1 | 12/2018 | Borras et al. |

(Continued)

FOREIGN PATENT DOCUMENTS

| CA | 2708627 A1 | 7/2009 |
|---|---|---|
| EP | 2311433 A2 | 4/2011 |

(Continued)

OTHER PUBLICATIONS

Gaudreault et al., Investigative Ophthalmology & Visual Science, Mar. 2012, vol. 53(14):3025.*
Tolentino et al., "Drugs in Phase II clinical trials for the treatment of age-related macular degeneration", Expert Opinion on Investigational Drugs, UK, (Sep. 22, 2014), vol. 24, No. 2, pp. 183-199, 2015.
"Monthly and As-Needed Treatment in the SHORE Study Resulted in Similar Visual Activity Gains in RVO", Retina today, (Sep. 1, 2014), pp. 14-17, Sep. 2014: URL: http://retinatoday.com/pdfs/rt0914_ASRS wrap up.pdf , (Apr. 6, 2016).

(Continued)

Primary Examiner — Xiaozhen Xie
(74) Attorney, Agent, or Firm — Xinsong Xu

(57) ABSTRACT

The present invention provides anti-VEGF antibodies formulated as high concentration, aqueous pharmaceutical compositions, suitable for an injection, preferably an intravitreal injection. The aqueous pharmaceutical compositions are useful for delivery of a high concentration of the antibody active ingredient to a patient without high levels of antibody aggregation and without a high level of sub-visible particulate matter. An aqueous composition of the invention comprises an antibody having a concentration of at least 50 mg/ml. An aqueous pharmaceutical composition of the invention includes a sugar, a buffering agent, and a surfactant.

14 Claims, 4 Drawing Sheets

Specification includes a Sequence Listing.

(56) References Cited

U.S. PATENT DOCUMENTS

| | | | |
|---|---|---|---|
| 2020/0172608 | A1 | 6/2020 | Borras et al. |
| 2020/0190179 | A1 | 6/2020 | Sigg et al. |
| 2021/0017266 | A1 | 1/2021 | Racine et al. |
| 2021/0340242 | A1 | 11/2021 | Gekkieva et al. |

FOREIGN PATENT DOCUMENTS

| | | | |
|---|---|---|---|
| WO | 2007/149334 | A2 | 12/2007 |
| WO | 2008150949 | A1 | 12/2008 |
| WO | 2009073160 | A1 | 6/2009 |
| WO | 2009155724 | A2 | 12/2009 |
| WO | 2012/097019 | A1 | 7/2012 |
| WO | 2013186700 | A1 | 12/2013 |
| WO | 2014005728 | A1 | 1/2014 |
| WO | 2014/093203 | A1 | 6/2014 |
| WO | 2014160490 | A1 | 10/2014 |
| WO | 2015166112 | A1 | 11/2015 |
| WO | 2016073915 | A1 | 5/2016 |
| WO | 2016073918 | | 5/2016 |
| WO | 2016085750 | | 6/2016 |

OTHER PUBLICATIONS

Pravin Dugel, "Novel molecule shows promise for future treatment of neovascular AMD", ASRS, 2014, San Diego, (Aug. 11, 2014); URL: http://www.healio.com/ophthalmology/retina-vitreous/news/online/%7B7ad33cbd-a2e0-49f1-a3f6-00fa79715708%7D/novel-molecule-shows-promise-for-future-treatment-ofneovascular-amd, (Apr. 6, 2016).

Jeffrey S Heier, "Intravitreal Aflibercept for AMD: 2-year Results", Retina Today, (Mar. 1, 2012), pp. 49-51; URL: http://retinatoday.com/pdfs/rt0312_feature_heier.pdf, (Apr. 6, 2016).

Pravin Dugel, "Results of ESBA 1008, a Single-Chain Antibody Fragment, for the Treatment of Neovascular AMD", URL:http://eyetube.net/series/daily-coverage-san-diego-august-2014/asile/, (Apr. 11, 2016), Video Only.

Daugherty, et al., "Formulation and delivery issues for monoclonal antibody therapeutics", Advanced Drug Delivery Reviews, 58, pp. 686-706 (2006).

Wang et al., "Antibody Structure, Instability, and Formulation", Journal of Pharmaceutical Sciences, vol. 96, No. 1, pp. 1-26 (2007).

Sgoutas et al., Effect of Lyophilization on Determinations of Lipoprotie(a), Serum. Clin. Chem., vol. 38, No. 7, pp. 1355-1360, 1992.

Wang, Lyophilization and development of solid protein pharmaceuticals, International Journal of Pharmaceutics, vol. 203, pp. 1-60, 2000.

Dugel et al., "Hawk and Harrier: Phase 3, Multicenter, Randomized, Double-Masked Trials of Brolucizumab for Neovascular Age-Related Macular Degeneration", American Academy of Ophthalmology, vol. 127, No. 1, Jan. 2020.

Yannuzzi et al., "Brolucizumab: evidence to date in the treatment of neovascular age-related macular degeneration", Clinical Ophthalmology, vol. 13, pp. 1323-1329, 2019.

Clinical Trial NCT04597632 publication dated Oct. 22, 2020, available at http://clinicaltrials.gov.

Clinical Trial NCT04543331 publication dated Sep. 10, 2020 available at http://clinicaltrials.gov.

Clinical Trial NCT04047472 publication dated Aug. 6, 2019 available at http://clinicaltrials.gov.

Clinical Trial NCT04679935 publication dated Feb. 2, 2021 available at http://clinicaltrials.gov.

Clinical Trial NCT04662944 publication dated Feb. 10, 2021 available at http://clinicaltrials.gov.

Clinical Trial NCT04287348 publication dated Aug. 14, 2021 available at http://clinicaltrials.gov.

Clinical Trial NCT05112835 publication dated Nov. 9, 2021, available at http://clinicaltrials.gov.

Hanns-Christian Mahler et al., Protein Aggregation: Pathways, Induction Factors and Analysis, Journal of Pharmaceutical Sciences, Sep. 29, 2008, 2909-2934, vol. 98, No. 9, Wiley Interscience.

Chen, et al., The influences of additives on the stability of interferon alfa in liquid state, Chinese Journal of New Drugs, 2008, 1425-1428, 17(16), English title and abstract only.

Cui, et al., Monoclonal antibodies: formulations of marketed products and recent advances in novel delivery system, Drug Development And Industrial Pharmacy, Jan. 22, 2017, 519-530, 43(4).

Steyaert, Cleaning validation of biologicals: Determination of a worst-case product for RTH 258, Advanced master Industrial Pharmacy, 2016-2017, 1-73.

Jorgensen, et al. Recent trends in stabilising peptides and proteins in pharmaceutical formulation—considerations in the choice of excipients, Expert Opinion on Drug Delivery, 6:11, Aug. 13, 2009, 1219-1230.

Mason, et al. "Effect of pH and Light on Aggregation and Conformation of an IgG1 mAb," Mol. Pharmaceuticals, 9, 774-790, 2012.

Wuchner et al., "Industry Perspective ont the use and Characterization of Polysorbates for Biopharmaceutical Products Part 1: Survey Report on Current State and Common Practices for Handling and Control of Polysorbates," Journal of Pharmaceutical Sciences, 111, 1280-1291, 2022.

Usach, et al. "Subcutaneous Injection of Drugs: Literature Review of Factors Influencing Pain Sensation at the Injection Site," Adv. Ther., 36:2986-2996, 2019.

Srivastava, et al. "Approaches to Alleviating Subcutaneous Injection-Ste Pain for Citrate Formulations," Pharmaceutical Technology, 32-37, Jun. 2020.

Agarkhed, et al. "Effect of Polysorbate 80 Concentration on Thermal and Photostability of a Monoclonal Antibody," AAPS PharmaSciTech, vol. 14, No. 1, 1-9, Mar. 2013.

Desai, et al. "An Intercompany Perpective on Practical Experiences of Predicting, Optimizing and Analyzing High Concentration Biologic Therapeutic Formulations," Journal of Pharmaceutical Sciences, 112, 359-369, 2023.

\* cited by examiner

STABLE PROTEIN SOLUTION FORMULATION CONTAINING HIGH CONCENTRATION OF AN ANTI-VEGF ANTIBODY

The present application is a divisional application of U.S. application Ser. No. 14/934,666, filed Nov. 6, 2015, now U.S. Pat. No. 10,689,438, which claims priority to U.S. Provisional Application Ser. No. 62/088,061, filed on Dec. 5, 2014, and to U.S. Provisional Application Ser. No. 62/076,770, filed on Nov. 7, 2014, the disclosures of which are specifically incorporated by reference herein.

FIELD OF THE INVENTION

The present invention relates to aqueous pharmaceutical formulations of anti-VEGF antibodies, a process for the preparation thereof, and uses of the formulations.

BACKGROUND OF THE INVENTION

Vascular endothelial growth factor (VEGF) is a known regulator of angiogenesis and neovascularization, and has been shown to be a key mediator of neovascularization associated with tumors and intraocular disorders (Ferrara et al. Endocr. Rev. 18:4-25 (1997)). The VEGF mRNA is overexpressed in many human tumors, and the concentration of VEGF in eye fluids are highly correlated to the presence of active proliferation of blood vessels in patients with diabetic and other ischemia-related retinopathies (Berkman et al., J Clin Invest 91:153-159 (1993); Brown et al. Human Pathol. 26:86-91 (1995); Brown et al. Cancer Res. 53:4727-4735 (1993); Mattern et al. Brit. J. Cancer. 73:931-934 (1996); and Dvorak et al. Am J. Pathol. 146:1029-1039 (1995); Aiello et al. N. Engl. J. Med. 331:1480-1487 (1994)). In addition, recent studies have shown the presence of localized VEGF in choroidal neovascular membranes in patients affected by AMD (Lopez et al. Invest. Ophtalmo. Vis. Sci. 37:855-868 (1996)). Anti-VEGF neutralizing antibodies can be used to suppress the growth of a variety of human tumor cell lines in nude mice and also inhibit intraocular angiogenesis in models of ischemic retinal disorders (Kim et al. Nature 362:841-844(1993); Warren et al. J. Clin. Invest 95:1789-1797 (1995); Borgstrom et al. Cancer Res. 56:4032-4039 (1996); and Melnyk et al. Cancer Res. 56:921-924 (1996)) (Adamis et al. Arch. Opthalmol. 114: 66-71 (1996)).

A number of antibodies are approved for therapeutic use in humans and other mammals, including anti-VEGF antibodies. The concentration of therapeutic antibodies in liquid pharmaceutical formulations varies widely depending, for example, on the route of administration. There is often a need for a high concentration formulation of an antibody when small volumes are desired. For example, high concentration formulations may be desirable for intravitreal injection or subcutaneous administration.

However, formulations with high concentration of antibody may have short shelf lives, and the formulated antibodies may lose biological activity caused by chemical and physical instabilities during storage. Aggregation, deamidation and oxidation are known to be the most common causes of antibody degradation. In particular, aggregation can potentially lead to increased immune response in patients, leading to safety concerns. Thus it must be minimized or prevented.

Formation of particulates in biotherapeutic formulations is also a major quality concern, as particulates in the tens of microns to sub-millimeter and millimeter size range can generally be seen by the naked human eye (see Das, 2012, AAPS PharmSciTech, 13:732-746). Particulates in therapeutic ophthalmic preparations can cause damage to the eye. Therefore, there are regulatory standards to ensure sub-visible particulate matter content in ophthalmic formulations is within certain limits. For example, the U.S. Pharmacopeial Convention (USP) has set requirements for particulate matter in ophthalmic solutions, such as the maximum number of particles >10 μm diameter is 50 per mL, the maximum number of particles ≥25 μm diameter is 5 per mL, and the maximum number of particles ≥50 μm diameter is 2 per mL determined by the microscopic method particle count (see USP General Chapter <789>).

Methods for producing high concentration antibody formulations are known. However, a universal approach does not exist to overcome the unpredictable impact of an antibody's amino acid sequence on its tendency to form aggregates or degrade in the presence of various pharmaceutical excipients, buffers, etc. Further, preparing an ophthalmic formulation with a high concentration of protein (such as an antibody) that contains an acceptable level of sub-visible particles is challenging and not predictable.

It is an object of the invention to provide further and improved formulations with high concentration of anti-VEGF antibodies and low levels of antibody aggregation and sub-visible particles, that are suitable for administration to a human, in particular to a human eye.

SUMMARY OF THE INVENTION

Accordingly, the present invention is directed to an aqueous pharmaceutical composition comprising a high concentration of anti-VEGF antibody suitable for ophthalmic injection. In certain aspects, the aqueous pharmaceutical compositions of the invention exhibit low to undetectable levels of antibody aggregation or degradation, with very little to no loss of the biological activities during manufacture, preparation, transportation and long periods of storage, the concentration of the anti-VEGF antibody being at least about 50 mg/ml, 60 mg/ml, 80 mg/ml, 100 mg/ml, 120 mg/ml, 140 mg/ml, 160 mg/ml, 180 mg/ml, or 200 mg/ml.

The invention provides aqueous pharmaceutical compositions comprising an anti-VEGF antibody, a stabilizer, a buffer, and a surfactant. In certain aspects, as aqueous pharmaceutical composition comprises: (i) at least 50 mg/ml of an anti-VEGF antibody, (ii) sucrose or trehalose as a stabilizer, (iii) a citrate or histidine buffer, and (iv) polysorbate 80 as a surfactant.

In certain aspects, the aqueous pharmaceutical composition comprises about 4.5%-11% w/v sucrose or 5%-10% trehalose, 0.006% to 0.012% citric acid (w/v), 0.2% to 0.6% trisodium citrate dihydrate (w/v), and about 0.01% to 0.1% polysorbate 80 (w/v), wherein the pH of the formulation is 6.3 to 7.3.

Specific preferred embodiments of the invention will become evident from the following more detailed description of certain preferred embodiments and the claims.

DETAILED DESCRIPTION OF THE INVENTION

Figure 1:
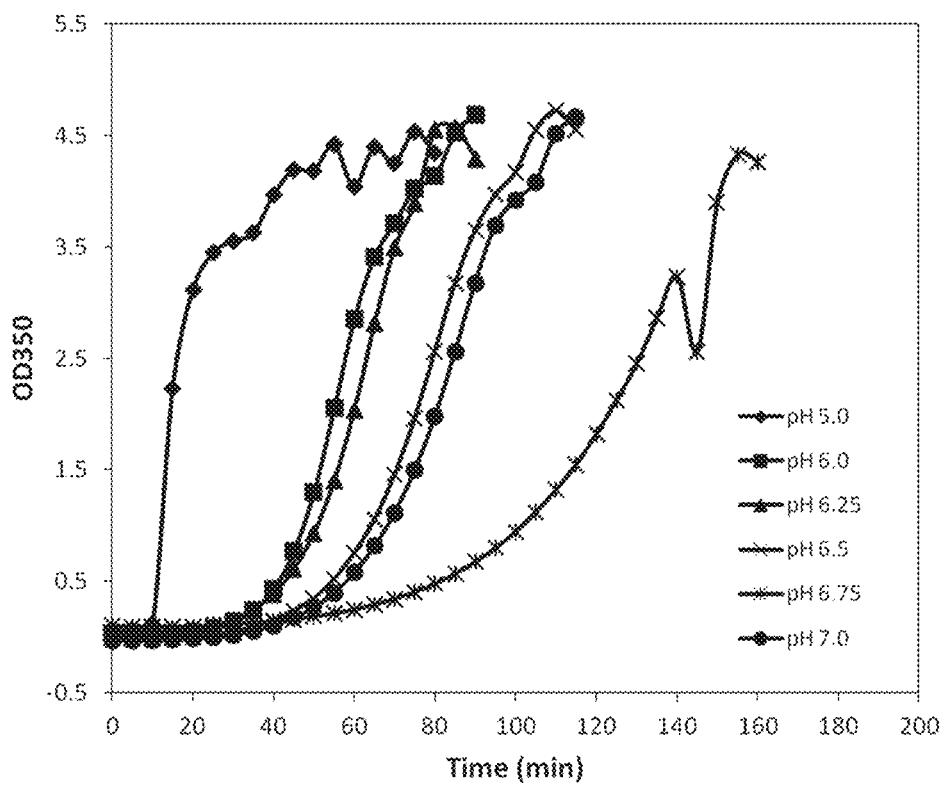
FIG. 1 shows a graph of the results from a turbidity assay for 1008 formulated at different pH. The x-axis shows the incubation time at 55° C.; while y-axis shows the optical density monitored at 350 nm.

The invention provides aqueous pharmaceutical compositions comprising a high concentration of an anti-VEGF antibody. In certain embodiments an aqueous pharmaceutical composition of the invention is stable for at least 18 months at 2-8° C. and is suitable for ocular administration, including injection or infusion. In a particular embodiment, an aqueous pharmaceutical composition of the invention meets the USP <789> requirements relative to the presence of particulate matter. Thus, in certain embodiments, the maximum number of particles ≥10 µm diameter in an aqueous pharmaceutical composition of the invention is 50 per mL, the maximum number of particles ≥25 µm diameter in an aqueous pharmaceutical composition of the invention is 5 per mL, and the maximum number of particles ≥50 µm diameter in an aqueous pharmaceutical composition of the invention is 2 per mL, said particle numbers being determined by the light obscuration and/or microscopic particle count method as required by the U.S. Pharmacopeial Convention General Chapter <789>).

As used herein, an "aqueous" pharmaceutical composition is a composition suitable for pharmaceutical use, wherein the aqueous carrier is distilled water. A composition suitable for pharmaceutical use may be sterile, homogeneous and/or isotonic. Aqueous pharmaceutical compositions may be prepared either directly in an aqueous form, for example in pre-filled syringe ready for use (the "liquid formulations") or as lyophilisate to be reconstituted shortly before use. As used herein, the term "aqueous pharmaceutical composition" refers to the liquid formulation or reconstituted lyophilized formulation. In certain embodiments, the aqueous pharmaceutical compositions of the invention are suitable for ophthalmic administration to a human subject. In a specific embodiment, the aqueous pharmaceutical compositions of the invention are suitable for intravitreal administration. In another embodiment, the aqueous pharmaceutical compositions of the invention are suitable for administration by intravitreal infusion.

The present invention provides novel pharmaceutical formulations, in particular novel pharmaceutical formulations in which the active ingredient comprises antibodies to human VEGF. In one aspect, the invention relates to an aqueous pharmaceutical composition with high concentration of anti-VEGF antibodies. Preferred anti-VEGF antibodies in formulations of the invention are described in WO 2009/155724, the entire contents of which are hereby incorporated by reference.

The term "antibody" as used herein includes whole antibodies and any antigen binding fragment (i.e., "antigen-binding portion," "antigen binding polypeptide," or "immunobinder") or single chain thereof. An "antibody" includes a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1 CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion") refers to one or more fragments of an antibody that retain the ability to specifically bind to an antigen (e.g., VEGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) *Nature* 341: 544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

In a preferred embodiment, an aqueous pharmaceutical composition of the invention comprises a variable heavy chain having the sequence as set forth in SEQ ID NO: 1 and a variable light chain having the sequence as set forth in SEQ ID NO: 2.

VH:

SEQ ID NO: 1

EVQLVESGGGLVQPGGSLRLSCTASGFSLTDYYYMTWVRQAPGKGLEWVG

FIDPDDDPYYATWAKGRFTISRDNSKNTLYLQMNSLRAEDTAVYYCAGGD

HNSGWGLDIWGQGTLVTVSS

VL:

SEQ ID NO: 2

EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN

FGQGTKLTVLG

In another preferred embodiment, the anti-VEGF antibody is a single-chain Fv (scFv) antibody fragment comprising the sequence:

(SEQ ID NO: 3)

EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN

FGQGTKLTVLGGGGSGGGGSGGGGSGGGGSEVQLVESGGGLVQPGGSLR

LSCTASGFSLTDYYYMTWVRQAPGKGLEWVGFIDPDDDPYYATWAKGRFT

ISRDNSKNTLYLQMNSLRAEDTAVYYCAGGDHNSGWGLDIWGQGTLVTVS

S

An anti-VEGF antibody in an aqueous pharmaceutical composition of the invention can be produced, for example, as described in WO 2009/155724. An scFv can be produced using an expression vector, as described therein. A methionine derived from the start codon in an expression vector is present in the final protein in cases where it has not been cleaved posttranslationally (see SEQ ID NO: 4 in the Examples).

In certain embodiments, the anti-VEGF antibody in an aqueous pharmaceutical composition of the invention comprises heavy chain CDR1, CDR2 and CDR 3 as set forth in SEQ ID NO: 5, 6, and 7 respectively, and light chain CDR1, CDR2 and CDR3 as set forth in SEQ ID NO: 8, 9, and 10.

SEQ ID NO: 5
GFSLTDYYYMT

SEQ ID NO: 6
FIDPDDDPYYATWAKG

SEQ ID NO: 7
GDHNSGWGLDI

SEQ ID NO: 8
QASEIIHSWLA

SEQ ID NO: 9
LASTLAS

SEQ ID NO: 10
QNVYLASTNGAN

In one embodiment, the concentration of an anti-VEGF antibody in the aqueous pharmaceutical composition of the invention is at least 50 mg/ml. Preferably, the aqueous pharmaceutical composition of the invention comprises about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, about 160 mg/ml, about 170 mg/ml, about 180 mg/ml, about 190 mg/ml, about 200 mg/ml, about 210 mg/ml, about 220 mg/ml, about 230 mg/ml, about 240 mg/ml, about 250 mg/ml or about 300 mg/ml of an anti-VEGF antibody.

In certain embodiments, the aqueous pharmaceutical composition of the invention comprises between 60 mg/ml and 120 mg/ml of an anti-VEGF antibody, for example, an antibody comprising SEQ ID NO: 1 and SEQ ID NO: 2.

In one embodiment, the aqueous pharmaceutical composition of the invention comprises 60 mg/ml of an anti-VEGF antibody comprising SEQ ID NO: 3.

In another embodiment, the aqueous pharmaceutical composition of the invention comprises 120 mg/ml of an anti-VEGF antibody comprising SEQ ID NO: 3.

The aqueous pharmaceutical compositions of the invention include, in addition to the anti-VEGF antibody, further components such as one or more of the following: (i) a stabilizer; (ii) a buffering agent; (iii) a surfactant; and (iv) a free amino acid. Inclusion of each of such additional components can give compositions with low aggregation of the anti-VEGF antibody. Preferably, the aqueous pharmaceutical compositions of the invention include, in addition to the anti-VEGF antibody: (i) a stabilizer; (ii) a buffering agent; and (iii) a surfactant.

Suitable stabilizer for use with the invention can act, for example, as viscosity enhancing agents, bulking agents, solubilizing agents, and/or the like. The stabilizer can be ionic or non-ionic (e.g. sugars). As sugars they include, but are not limited to, monosaccharides, e.g., fructose, maltose, galactose, glucose, D-mannose, sorbose and the like; disaccharides, e.g. lactose, sucrose, trehalose, cellobiose, and the like; polysaccharides, e.g. raffinose, melezitose, maltodextrins, dextrans, starches, and the like; and alditols, such as mannitol, xylitol, maltitol, lactitol, xylitol sorbitol (glucitol) and the like. For example, the sugar may be sucrose, trehalose, raffinose, maltose, sorbitol or mannitol. The sugar may be a sugar alcohol or an amino sugar. Sucrose and trehalose are preferred. Most preferred is sucrose. As ionic stabilizer they may include salts such as NaCl or amino acid components such as arginine-HCl.

Suitable buffering agents for use with the invention include, but are not limited to, organic acid salts such as salts of citric acid, ascorbic acid, gluconic acid, carbonic acid, tartaric acid, succinic acid, acetic acid or phthalic acid; Tris, thomethamine hydrochloride, or phosphate buffer. In addition, amino acid components can also be used as buffering agent. Citrate or histidine buffer are particularly useful, including 10-20 mM of histidine buffer, for example, 0.13% to 0.26% (w/v) histidine and 0.03%-0.07% (w/v) histidine Hydrochloride monohydrate), or 10-20 mM citrate buffer, for example 0.006% to 0.012% citric acid (w/v) and 0.2% to 0.6% trisodium citrate dihydrate (w/v). Citric acid used in a formulation of the invention can be any hydration form, for example anhydrous or monohydrate.

The aqueous pharmaceutical compositions include such buffering agent or pH adjusting agent to provide improved pH control. In certain embodiment, an aqueous pharmaceutical composition of the invention has a pH between 5.0 and 8.0, between 5.0 and 7.0, between 6.0 and 8.0, or between 6.0 and 7.0. In one embodiment, the pH of an aqueous pharmaceutical composition of the invention is about 6.3 to about 7.3. In a specific embodiment, an aqueous pharmaceutical composition of the invention has a pH of about 6.8.

As used herein, the term "surfactant" herein refers to organic substances having amphipathic structures; i.e., they are composed of groups of opposing solubility tendencies, typically an oil-soluble hydrocarbon chain and a watersoluble ionic group. Surfactants can be classified, depending on the charge of the surface-active moiety, into anionic, cationic and dispersing agents for various pharmaceutical compositions and preparations of biological materials.

Suitable surfactants for use with the invention include, but are not limited to, non-ionic surfactants, ionic surfactants and zwitterionic surfactants. Typical surfactants for use with the invention include, but are not limited to, sorbitan fatty acid esters (e.g. sorbitan monocaprylate, sorbitan monolaurate, sorbitan monopalmitate), sorbitan trioleate, glycerine fatty acid esters (e.g. glycerine monocaprylate, glycerine monomyristate, glycerine monostearate), polyglycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxyethylene polyoxypropylene alkyl ethers (e.g. polyoxyethylene polyoxypropylene glycol, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearic acid amide); $C_{10}$-$C_{18}$ alkyl sulfates (e.g. sodium cetyl sulfate, sodium lauryl sulfate, sodium oleyl sulfate), polyoxyethylene $C_{10}$-$C_{18}$ alkyl ether sulfate with an average of 2 to 4 moles of ethylene oxide units added (e.g. sodium polyoxyethylene lauryl sulfate), and $C_1$-$C_{18}$ alkyl sulfosuccinate ester salts (e.g. sodium lauryl sulfosuccinate ester); and natural surfactants such as lecithin, glycerophospholipid, sphingophospholipids (e.g. sphingomyelin), and sucrose esters of $C_{12-18}$ fatty acids. A composition may include one or more of these surfactants. Preferred surfactants are polyoxyethylene sorbitan fatty acid esters e.g. polysorbate 20, 40, 60 or 80. Polysorbate 80 is particularly preferred.

Suitable free amino acids for use with the invention include, but are not limited to, arginine, lysine, histidine, ornithine, isoleucine, leucine, alanine, glycine glutamic acid or aspartic acid. The inclusion of a basic amino acid is preferred i.e. arginine, lysine and/or histidine. If a composition includes histidine then this may act both as a buffering agent and a free amino acid, but when a histidine buffer is used it is typical to include a non-histidine free amino acid e.g. to include histidine buffer and lysine. An amino acid may be present in its D- and/or L-form, but the L-form is typical. The amino acid may be present as any suitable salt e.g. a hydrochloride salt, such as arginine-HCl. In one preferred embodiment, an aqueous pharmaceutical composition of the invention does not comprise any such free amino acids.

In a preferred embodiment, a sugar is present in the aqueous pharmaceutical composition of the invention, e.g. after reconstitution of a lyophilisate in water, at a concentration of between 3 and 11% (w/v). In certain embodiments, the sugar is sucrose at a concentration of about 4.5% to about 11%, or trehalose at a concentration of about 5% to about 10%. A concentration of 6.75% (w/v) sucrose is preferred.

In a preferred embodiment, a buffering agent is present in the aqueous pharmaceutical composition of the invention, e.g. after reconstitution of a lyophilisate in water, at a concentration of between 1 and 60 mM e.g. 10-40 mM, 15-30 mM, 15-25 mM. In certain embodiments, the buffering agent is citrate or histidine. A concentration of 15 mM citrate buffer is preferred.

In a preferred embodiment, a surfactant is present in the aqueous pharmaceutical composition of the invention, e.g. after reconstitution of a lyophilisate in water, at a concentration of up to 0.2% (by volume) e.g. 0.01-0.1%, 0.03-0.08%, 0.04-0.08%. A concentration of 0.05% polysorbate 80 is preferred.

Other contemplated excipients, which may be utilized in the aqueous pharmaceutical compositions of the invention include, for example, antimicrobial agents, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, 4th edition, Rowe et al., Eds., American Pharmaceuticals Association (2003); and Remington: the Science and Practice of Pharmacy, $21^{st}$ edition, Gennaro, Ed., Lippincott Williams & Wilkins (2005).

Preferred formulations of the invention are shown in Table 40 in the Examples below.

In certain embodiments, lyophilisation of an anti-VEGF antibody is contemplated to provide an aqueous pharmaceutical composition of the invention for treating a patient.

Techniques for lyophilisation of antibodies are well known in the art e.g. see John F. Carpenter and Michael J. Pikal, 1997 (*Pharm. Res.* 14, 969-975); Xialin (Charlie) Tang and Michael J. Pikal, 2004 (*Pharm. Res.* 21, 191-200).

Before a lyophilisate can be administered to a patient it should be reconstituted with an aqueous reconstituent. This step permits antibody and other components in the lyophilisate to re-dissolve to give a solution which is suitable for injection to a patient.

The volume of aqueous material used for reconstitution dictates the concentration of the antibody in a resulting pharmaceutical composition. Reconstitution with a smaller volume of reconstituent than the pre-lyophilisation volume provides a composition which is more concentrated than before lyophilisation. The reconstitution factor (volume of formulation after lyophilization:volume of formulation before lyophilization) may be from 1:0.5 to 1:6. A reconstitution factor of 1:3 is useful. As mentioned above, lyophilisates of the invention can be reconstituted to give aqueous compositions with an anti-VEGF antibody concentration of at least 50 mg/ml (i.e., at least 60, 70, 80, 90, 100, 110, 120, or 130 mg/ml), and the volume of reconstituent will be selected accordingly. If required, the reconstituted formulation can be diluted prior to administration to a patient as appropriate to deliver the intended dose.

Typical reconstituents for lyophilized antibodies include sterile water or buffer, optionally containing a preservative. If the lyophilisate includes a buffering agent then the reconstituent may include further buffering agent (which may be the same as or different from the lyophilisate's buffering agent) or it may instead include no buffering agent (e.g. WFI (water for injection), or physiological saline).

The aqueous pharmaceutical compositions of the invention comprising anti-VEGF antibodies can be used to treat a variety of diseases or disorders. Pharmaceutical compositions comprising anti-VEGF antibodies are particularly useful to treat neovascular ocular diseases in a subject.

A "neovascular ocular disease" that can be treated using an aqueous pharmaceutical composition of the invention includes, a condition, disease, or disorder associated with ocular neovascularization, including, but not limited to, abnormal angiogenesis, choroidal neovascularization (CNV), retinal vascular permeability, retinal edema, diabetic retinopathy (particularly proliferative diabetic retinopathy), diabetic macular edema, neovascular (exudative) age-related macular degeneration (AMD), including CNV associated with nAMD (neovascular AMD), sequela associated with retinal ischemia, Central Retinal Vein Occlusion (CRVO), and posterior segment neovascularization.

The aqueous pharmaceutical compositions of the invention may include further active ingredients in addition to the anti-VEGF antibody. Further pharmacological agents may include, for instance, other antibodies useful for treating ocular diseases.

Aqueous pharmaceutical compositions of the invention can be administered to a patient. As used herein, the term "subject" or "patient" refers to human and non-human mammals, including but, not limited to, primates, rabbits, pigs, horses, dogs, cats, sheep, and cows. Preferably, a subject or patient is a human.

Administration will typically be via a syringe. Thus the invention provides a delivery device (e.g. a syringe) including a pharmaceutical composition of the invention (e.g., pre-filled syringe). Patients will receive an effective amount of the anti-VEGF antibody as the principal active ingredient (i.e., an amount that is sufficient to achieve or at least partially achieve the desired effect). A therapeutically effective dose is sufficient if it can produce even an incremental change in the symptoms or conditions associated with the disease. The therapeutically effective dose does not have to completely cure the disease or completely eliminate symptoms. Preferably, the therapeutically effective dose can at least partially arrest the disease and its complications in a patient already suffering from the disease. Amounts effective for this use will depend upon the severity of the disorder being treated and the general state of the patient's own immune system.

The dose amount can be readily determined using known dosage adjustment techniques by a physician having ordinary skill in treatment of the disease or condition. The therapeutically effective amount of an anti-VEGF antibody used in an aqueous pharmaceutical composition of the invention is determined by taking into account the desired dose volumes and mode(s) of administration, for example. Typically, therapeutically effective compositions are administered in a dosage ranging from 0.001 mg/ml to about 200 mg/ml per dose. Preferably, a dosage used in a method of the invention is about 60 mg/ml to about 120 mg/ml (i.e., about 60, 70, 80, 90, 100, 110, or 120 mg/ml). In a preferred embodiment, the dosage of an anti-VEGF antibody used in a method of the invention is 60 mg/ml or 120 mg/ml.

In certain embodiments, a dose is administered directly to an eye of a patient. In one embodiment, a dose per eye is at least about 0.5 mg up to about 6 mg. Preferred doses per eye include about 0.5 mg, 0.6 mg, 0.7 mg, 0.8 mg, 0.9 mg, 1.0 mg, 1.2 mg, 1.4 mg, 1.6 mg, 1.8 mg, 2.0 mg, 2.5 mg, 3.0 mg, 3.5 mg, 4.0 mg, 4.5 mg, 5.0 mg, 5.5 mg, and 6.0 mg. Doses can be administered in various volumes suitable for ophthalmic administration, such as 50 µl or 100 µl, for example, including 3 mg/50 µl or 6 mg/50 µl. Smaller volumes can also be used, including 10 µl or less, for example about 10 µl or about 8.0 µl. In certain embodiments, a dose of 1.2 mg/10 µl or 1 mg/8.0 µl (e.g., 1 mg/8.3 µl) is delivered to an eye of a patient for treating or ameliorating one or more of the diseases and disorders described above. Delivery can be, for example, by intravitreal injection or infusion.

The invention also provides formulations (i.e., aqueous pharmaceutical compositions) of the invention for use as medicaments, e.g. for use in delivering an antibody to a patient, or for use in treating or ameliorating one or more of the diseases and disorders described above.

The invention further provides a method for delivering an anti-VEGF antibody to a patient, comprising a step of administering to the patient an aqueous pharmaceutical composition of the invention.

In certain embodiments, a method for delivering an anti-VEGF antibody to a patient invention comprises the steps of: (i) reconstituting a lyophilisate of the invention to give an aqueous formulation, and (ii) administering the aqueous formulation to the patient. Step (ii) ideally takes place within 24 hours of step (i) (e.g., within 12 hours, within 6 hours, within 3 hours, or within 1 hour). Certain specific embodiments of the invention are described as numbered hereafter:

1. An aqueous pharmaceutical composition, comprising (i) at least 50 mg/ml of an anti-VEGF antibody that includes heavy chain CDR1, CDR2 and CDR3 of SEQ ID NO: 5, 6, and 7 respectively, and light chain CDR1, CDR2 and CDR3 of SEQ ID NO: 8, 9, and 10 respectively, (ii) sucrose or trehalose, (iii) a citrate or histidine buffer, and (iv) polysorbate 80 as a surfactant.

2. The aqueous pharmaceutical composition of Embodiment 1, comprising 4.5% to 11% (w/v) sucrose or 5% to 10% trehalose, 0.006% to 0.012% citric acid (w/v), 0.2% to 0.6% trisodium citrate dihydrate (w/v), and 0.01% to 0.1% polysorbate 80 (w/v), wherein the pH of the composition is about 6.3 to about 7.3.

3. The aqueous pharmaceutical composition of Embodiment 2, wherein the concentration of sucrose is 6.75% (w/v) the concentration of citric acid is about 0.01% (w/v), the concentration of trisodium citrate dihydrate is about 0.428% (w/v), the concentration of polysorbate 80 is about 0.05% (w/v), and the pH is about 6.8.

4. The aqueous pharmaceutical composition of any one of Embodiments 1-3, wherein the concentration of the anti-VEGF antibody is at least 60 mg/ml, at least 70 mg/ml, at least 80 mg/ml, at least 90 mg/ml, at least 100 mg/ml, at least 110 mg/ml, at least 120 mg/ml, at least 130 mg/ml, at least 140 mg/ml, or at least 150 mg/ml.

5. The aqueous pharmaceutical composition of any one of Embodiments 1-4, wherein the concentration of the anti-VEGF antibody is about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, or about 150 mg/ml.

6. The aqueous pharmaceutical composition of any one of Embodiments 1-5, wherein the anti-VEGF antibody comprises the sequences of SEQ ID NO: 1 and SEQ ID NO: 2.

7. The aqueous pharmaceutical composition of any one of Embodiments 1-6, wherein the anti-VEGF antibody comprises the sequence of SEQ ID NO: 3.

8. The aqueous pharmaceutical composition of any one of Embodiments 1-7, wherein the concentration of the anti-VEGF antibody is about 60 mg/ml or about 120 mg/ml.

9. A delivery device including the aqueous pharmaceutical composition of any one of Embodiments 1-8.

10. The delivery device of Embodiment 9, which is a pre-filled syringe.

11. A method for delivering an anti-VEGF antibody to a subject, comprising a step of administering to the subject an aqueous pharmaceutical composition of any one of Embodiments 1-8.

12. A method of treating an ocular disease or disorder that is mediated by VEGF, comprising administering to a subject, an aqueous pharmaceutical composition of any one of Embodiments 1-8.

13. The method of Embodiment 12, wherein said ocular disease or disorder that is an ocular neovascular disease.

14. A lyophilized formulation prepared by lyophilizing the aqueous pharmaceutical composition of any one of Embodiments 1-8.

15. A method for preparing a lyophilisate, comprising the steps of: (i) preparing an aqueous solution of an anti-VEGF antibody, sucrose or trehalose, citrate or histidine buffer, and a surfactant; and (ii) lyophilizing the aqueous solution.

16. The method of Embodiment 15, wherein the anti-VEGF antibody includes heavy chain CDR1, CDR2 and CDR3 of SEQ ID NO: 5, 6, and 7 respectively, and light chain CDR1, CDR2 and CDR3 of SEQ ID NO: 8, 9, and 10 respectively.

17. The method of Embodiment 16, wherein the anti-VEGF antibody comprises the sequences of SEQ ID NO: 1 and SEQ ID NO: 2.

18. The method of any one of Embodiments 16-17, wherein the anti-VEGF antibody comprises the sequence of SEQ ID NO: 3.

19. An aqueous pharmaceutical composition of any one of Embodiments 1-8 for use in delivering an anti-VEGF antibody to a subject, comprising a step of administering the aqueous pharmaceutical composition to the subject.

20. An aqueous pharmaceutical composition of any one of Embodiments 1-8 for use in treating an ocular disease or disorder that is mediated by VEGF, comprising administering the aqueous pharmaceutical composition to a subject.

21. The use of Embodiment 20, wherein said ocular disease or disorder that is an ocular neovascular disease.

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

The contents of any patents, patent applications, and references cited throughout this specification are hereby incorporated by reference in their entireties.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

EXAMPLES

The following examples describe formulation development efforts designed to identify suitable stabilization approaches and compositions to provide stable, highly concentrated solutions comprising the antibody 1008, enabling an IVT formulation with at least an 18-month shelf-life at refrigerated storage conditions that meets the regulatory requirements for ophthalmic products.

The 1008 antibody is a single-chain antibody that binds to and inhibits the biologic activity of human vascular endothelial growth factor A (VEGF-A). The amino acid sequence of expressed 1008 is:

```
                                               (SEQ ID NO: 4)
MEIVMTQSPS TLSASVGDRV IITCQASEII HSWLAWYQQK

PGKAPKLLIY LASTLASGVP SRFSGSGSGA EFTLTISSLQ

PDDFATYYCQ NVYLASTNGA NFGQGTKLTV LGGGGSGGG

GSGGGGSGGG GSEVQLVESG GGLVQPGGSL RLSCTASGFS

LTDYYYMTWV RQAPGKGLEW VGFIDPDDDP YYATWAKGRF

TISRDNSKNT LYLQMNSLRA EDTAVYYCAG GDHNSGWGLD

IWGQGTLVTV SS
```

Significant amounts of sub-visible particulates were observed at a concentration of 60 mg/ml 1008 when 1008 was formulated as an isotonic solution in 15 mM citrate buffer with 0.001% polysorbate 20 at pH 6.25. The major issue with this initial formulation was the particulate matter exceeding regulatory limits for ophthalmic solutions for injection (USP<789>), even when stored at −20° C.

The following examples summarize the formulation development of 60 and 120 mg/ml 1008 intravitreal (IVT) solutions stable at 2-8° C. storage for at least 18 months. The formulation development effort focused on inhibition of the formation of sub-visible particles and meeting the USP requirement for content, purity and potency.

ANALYTICAL METHODS

The following methods were used throughout the Examples as indicated.

Micro-Flow Imaging (MFI) Method

MFI method used for analysis of excipient screening, Study 1 and Study 2 for 60 mg/ml optimization studies was as follows:
Total sample volume used: 0.50 mL
Purge volume: 0.20 mL
Analysis volume: 0.26 mL The optimize illumination step was performed with purified filtered particle free water. WFI method used for analysis of 120 mg/ml 1008 Study 3 and Study 4:
Total sample volume used: 0.80 mL
Purge volume: 0.23 mL
Analysis volume: 0.48 mL The optimize illumination step was performed with purified filtered particle free water.

SEC method

SE-HPLC (Size exclusion chromatography) separates proteins according to their size. Separation was achieved by the differential exclusion, or inclusion, of the sample molecules as they passed through the porous-particle stationary phase. High performance liquid chromatography system capable of maintaining a flow rate of 0.25 ml/minute and a sample temperature of 4° C., equipped with a TOSOH SuperSW3000 column (Tosoh Bioscience LLC, King of Prussia, PA), and a detector capable of operating at 214 nm and 280 nm simultaneously. This method was used for purity testing.

IEX-HPLC Method

AIEX-HPLC (Anion exchange high performance liquid chromatography) separates proteins according to their net charge. This procedure was performed using high-performance liquid chromatography (HPLC), capable of maintaining a flow rate of 0.8 ml/minute, with a temperature controlled column compartment (set at 25° C.) containing a strong anion exchange column, an auto-sampler (set at 4° C.), and a variable wavelength UV detector, capable of operating at 280 nm.

CGE Method

The capillary gel electrophoresis method was performed for the determination of the identity and purity of proteins between the molecular weights of 10 kDa and 225 kDa by SDS gel Capillary Electrophoresis. The capillary was dynamically filled with a Beckman Coulter 0.2% SDS Gel Buffer, pH 8, proprietary formulation. The separation of the protein was performed by molecular sieving electrophoresis. The logarithm of protein molecular weight was linear with its reciprocal electrophoretic mobility. The identity of a protein was determined by comparing its migration with a molecular weight standard. The purity was determined by area percent analysis of the parent peak and impurities. A photodiode array detector (PDA) was used to analyze the sample at 220 nm.

Potency Analysis

The competition ELISA was used for potency testing. Competitive ELISA, the ability of 1008 to compete with VEGFR2/Fc for biotinylated VEGF was measured. The signal observed was inversely related to the concentration of 1008, as increasing amounts of 1008 effectively blocked the binding of biotinylated VEGF with its receptor VEGFR2/Fc. Each sample was analyzed in a 96-well microtiter plate against a 1008 reference standard, and the relative potency of the sample to that of the reference standard was reported.

Example 1

Excipient Screening 1008 was formulated in a citrate buffer at pH 6.25. The formulation composition is shown in Table 1.

TABLE 1

| Component | Concentration (W/V %) |
|---|---|
| 1008 | 6% |
| Trisodium Citrate (Dihydrate) | 0.59% |
| Sodium Chloride | 0.73% |
| Polysorbate 20 | 0.001% |
| Hydrochloric Acid | pH 6.25 |
| Water For Injection | Qs 100 |

Significant numbers of sub-visible particulates were observed in the above formulation. The particulate matter exceeded regulatory limits for ophthalmic solutions for injection USP<789> even in the storage of −20° C.

The effect of various excipients on formation of sub-visible particulates was investigated to develop a more stable liquid solution of 1008. The protein solutions at 60 mg/ml containing different excipients were stored at 40° C. and analyzed for particulates in the size of 1-100 µm by MFI. The experimental data demonstrated that most excipients tested, including arginine, dextran, ascorbic acid, methionine, and ammonium acetate, did not reduce the formation of the particulates. Only in presence of non-reducing sugars, such as sucrose and trehalose, was particulate formation significantly reduced.

Further excipient screening was conducted. Effect of excipients on 1008 stability was evaluated in ~60 mg/ml 1008 solution. Protein solutions containing 0.1% human serum albumin (HSA), 0.1% poloxamer 407, 0.1% Brij 35, 3% glycerin, 50 mM glycine were stored at 40° C., and the samples were assayed by MFI, SEC and IEX after 8, 21, and 28 days of storage. The results are shown in Table 2. The experimental data demonstrated the instability of the protein in the presence of the tested excipients.

TABLE 2

Results of Excipient Screening

| | Excipient | | | | |
|---|---|---|---|---|---|
| | 0.1% HSA | 0.1% Poloxamer 407 | 0.1% Brij 35 | 3% Glycerin | 50 mM Glycine |
| Time (day) | | | 8 | | |
| ≥10 um by MFI | 19 | 8 | 18 | 329 | 47 |
| ≥25 um by MFI | 5 | 5 | 6 | 43 | 8 |
| ≥50 um by MFI | 1 | 0 | 1 | 3 | 0 |
| Total by MFI | 538 | 381 | 378 | 24805 | 2436 |
| SEC (% initial) | 96.2 | 95.5 | 81.8 | 96.3 | 95.8 |
| IEX (% initial) | 95.1 | 94.3 | 82.7 | 95.0 | 95.6 |
| Time (day) | | | 21 | | |
| ≥10 um by MFI | 30 | 5 | 12 | 95 | 36 |
| ≥25 um by MFI | 7 | 0 | 5 | 14 | 10 |
| ≥50 um by MFI | 1 | 0 | 0 | 2 | 1 |
| Total by MFI | 495 | 197 | 1091 | 5622 | 1037 |
| SEC (% initial) | 88.2 | 87.7 | 63.2 | 89.4 | 89.4 |
| IEX (% initial) | 87.8 | 86.1 | 63.2 | 87.9 | 87.1 |
| Time (day) | | | 28 | | |
| ≥10 um by MFI | 69 | 382 | 595 | 365 | 466 |
| ≥25 um by MFI | 21 | 39 | 68 | 65 | 72 |
| ≥50 um by MFI | 5 | 4 | 6 | 9 | 15 |
| Total by MFI | 505 | 7718 | 2208 | 10690 | 52375 |
| SEC (% initial) | 85.7 | 84.7 | 65.3 | 86.1 | 84.5 |
| IEX (% initial) | 82.7 | 80.9 | 60.0 | 83.4 | 82.3 |

Stability of 57 mg/ml 1008 was investigated in 20 mM in phosphate buffer at pH6.25. The formulation containing 9% sucrose and 0.1% PS80 was assayed at 6, 14 and 27 days after storage at 40° C. The results are listed in Table 3.

TABLE 3

Stability of 57 mg/ml 1008 in 20 mM phosphate buffer

| Time at 40° C. (day) | 6 | 14 | 27 |
|---|---|---|---|
| ≥10 um by MFI (#/mL) | 43 | 42 | 11 |
| ≥25 um by MFI (#/mL) | 3 | 13 | 3 |
| ≥50 um by MFI (#/mL) | 1 | 4 | 0 |
| Total by MFI (#/mL) | 1418 | 1650 | 425 |
| SEC (% initial) | 97.3 | 91.9 | 82.1 |
| IEX (% initial) | 98.3 | 92.2 | 79.2 |

Example 2

New Formulation Development

Study 1
Excipient Screening

Protein solution of 60 mg/ml 1008 in 20 mM citrate buffer containing 0.001% polysorbate 20 and 0.73% NaCl at pH 6.25 was used for sample preparation. In order to remove the surfactant in the original protein solution, buffer exchange using NAP-25 column was first performed using the vehicle without polysorbate 20. The exchanged protein solution was then concentrated to about 60 mg/ml using Vivaspin filter with 10kDa MWCO. The excipients of HSA, glycine, glycerin, poloxamer 407, and Brij 35 were spiked individually. The prepared samples were then syringe-filtered through 0.2 um PVDF membrane to a 4 mL clear glass vial. About 100

µL sample was used for initial assay, while the rest of the samples were stored at 40° C. One milliliter sample of each formulation was pulled at 8, 21, and 28 days following storage at 40° C. for analysis by MF SEC and IEX.

Component Selection of Buffer, Sugar and Surfactant

Based on excipient screening studies performed internally, two buffers (citrate and histidine), sugars (sucrose and trehalose), and surfactants (Polysorbate 20 and Polysorbate 80) were selected for formulation component selection. Buffer strength of 20 mM, sugar concentration of 264 mM, and surfactant concentration of 0.1% were chosen for the study. A full factorial experimental study was designed as shown in the table below.

TABLE 4

Factors and Design for Study 1

| Factor | Design |
|---|---|
| Buffer | 20 mM Citrate or 20 mM Histidine |
| Sugar | 264 mM (9%) Sucrose or 264 mM (9%) Trehalose |
| Surfactant | 0.1% Polysorbate 20 or 0.1% Polysorbate 80 |

The full design used is shown in Table 5 below:

TABLE 5

Three Factors Full Factorial Design for Study 1

| No | Buffer (mM) | Sugar | Surfactant |
|---|---|---|---|
| 1 | 20 mM Citrate | 264 mM Trehalose | 0.1% PS 20 |
| 2 | 20 mM Citrate | 264 mM Trehalose | 0.1% PS 80 |
| 3 | 20 mM Citrate | 264 mM Sucrose | 0.1% PS 20 |
| 4 | 20 mM Citrate | 264 mM Sucrose | 0.1% PS 80 |
| 5 | 20 mM Histidine | 264 mM Trehalose | 0.1% PS 20 |
| 6 | 20 mM Histidine | 264 mM Trehalose | 0.1% PS 80 |
| 7 | 20 mM Histidine | 264 mM Sucrose | 0.1% PS 20 |
| 8 | 20 mM Histidine | 264 mM Sucrose | 0.1% PS 80 |

Other parameters:

| | |
|---|---|
| Concentration/pH | 50-60 mg/ml 1008 at pH 6.25 |
| Buffer Exchange | NAP25 column, concentrate with Vivaspin 10 kDa MWCO |
| Sample Size/Pkg | 2-2.5 mL in a 4 mL clear glass vial with a screw cap |
| Storage/Pull | 40° C./0, 1, 2 and 4 weeks |
| Assays | MFI, SEC and IEX |

Protein solution of 60 mg/ml 1008 in the original buffer containing 0.001% polysorbate 20 was used for the sample preparation. Four new vehicle buffers with different buffer/sugar combinations (20 mM Citrate/264 mM Trehalose, 20 mM Citrate/264 mM Sucrose, 20 mM Histidine/264 mM Trehalose, 20 mM Histidine/264 mM Sucrose) were prepared. 1008 drug substance (DS) was first exchanged into the vehicle buffers using Illustra NAP-25 column (GE Healthcare). The column was equilibrated with 25 mL of citrate buffer. Then 2 mL of 1008 DS was loaded onto the column. After the DS solution completed moved into the column, the column was washed with 2 mL of the same buffer used to equilibrate the column. The 6 mL solution eluted from the column was collected in a Vivaspin 6 concentrator (10KD MWCO, GE Healthcare). The 6 mL eluted solution was then concentrated to about 2 mL using a Beckman GS-15R centrifuge at 9384 ×g and 4° C. The concentration of protein was then measured with a NanoDrop 1000 spectrophotometer using OD280. Polysorbate 20 (PS20) or Polysorbate 80 (PS80) was spiked into the formulations to a final concentration of 0.1%. The prepared formulations were then filtered through 0.2 um PVDF syringe filter and filled into a 4 mL clear glass vial. About 100 uL sample was used for initial assay, while rest of the samples was stored at 40° C. One milliliter sample was pulled following storage of 1, 2 and 4 weeks at 40° C. for analysis by MFI, SEC and IEX.

The qualitative study was conducted in order to select the optimum sugar/surfactant/buffer components for the formulation. Two buffers (citrate and histidine), sugars (sucrose and trehalose), surfactants (Polysorbate 20 and Polysorbate 80) were used in the study design as discussed above. Four weeks stability study was conducted under the accelerated conditions (40° C.). The stability samples were assayed by SEC, IEX and MFI. Table 6 shows the stability results by SEC, IEX and melting point (Tm) by µDSC.

TABLE 6

Qualitative analysis of factors for 60 mg/ml 1008 at 40° C.

| No | 1 week/ 40° C. (SEC)* | 2-week/ 40° C. (SEC) | 4-week/ 40° C. (SEC) | 1 week/ 40° C. (IEX)* | 2-week/ 40° C. (IEX) | 4-week/ 40° C. (IEX) | Tm (° C.) by µDSC |
|---|---|---|---|---|---|---|---|
| 1 | 2.9 | 10.7 | 26.6 | 5.0 | 13.7 | 20.2 | 71.53 |
| 2 | 2.4 | 7.8 | 18.3 | 4.2 | 10.5 | 13.6 | 71.97 |
| 3 | 2.9 | 11.1 | 27.1 | 4.9 | 13.2 | 17.5 | 71.41 |
| 4 | 2.3 | 7.5 | 20.9 | 4.1 | 10.6 | 11.7 | 71.97 |
| 5 | 3.2 | 11.7 | 26.8 | 5.6 | 14.7 | 23.4 | 71.66 |
| 6 | 2.7 | 8.1 | 19.1 | 5.1 | 12.1 | 19.9 | 72.28 |
| 7 | 3.5 | 13.2 | 31.4 | 6.1 | 16.4 | 25.2 | 71.53 |
| 8 | 2.8 | 8.6 | 21.2 | 5.4 | 13.1 | 15.1 | 72.15 |

*% Loss using relative peak area

The stability results were analyzed using Minitab (Minitab Inc., State College PA). Since SEC and IEX showed the same trend, only SEC data were analyzed and reported by Minitab. The SEC results demonstrated surfactant was the only significant factor; the other factors that appeared to impact the response included buffer selection and interaction between buffer and sugar (to a less extent). SEC data suggested the optimum formulation component being citrate as buffer, polysorbate 80 as surfactant and sucrose as sugar.

Experimental results on particulates by MFI were also analyzed by Minitab. All the three factors evaluated (sugar, surfactant, and buffer) appeared to be insignificant ($\alpha=0.05$). Comparing the main effects on particulates, citrate was better than histidine; PS80 was better than PS20; Sucrose was similar or slightly better than trehalose. Therefore, citrate as buffer, polysorbate 80 as surfactant and sucrose as sugar were chosen for further studies.

Study 2

Optimization of Concentrations for Buffer, Sugar and Surfactant

A full factorial study containing three factors at two levels with two center points were performed in citrate and histidine buffers respectively, in order to determine the optimum concentration for each selected formulation component. The three factors are buffer (citrate or histidine), polysorbate 80 and sucrose. Factors and design space are tabulated in Table 7 and the detailed experimental designs are shown in Tables 8 and 9.

TABLE 7

Factors and Design Study 2

| Factor | Design | |
|---|---|---|
| Citrate buffer | 10-20 mM | NA |
| Histidine buffer | NA | 10-20 mM |
| Polysorbate 80 | 0.001-0.1% | 0.001-0.1% |
| Sucrose | 4.5-9% | 4.5-9% |

TABLE 8

Full Factorial Design in Citrate Buffer

| Run Order | Buffer (mM) | Sucrose (%) | Polysorbate 80 (%) |
|---|---|---|---|
| C1 | 10 | 4.5 | 0.001 |
| C2 | 20 | 4.5 | 0.001 |
| C3 | 10 | 9 | 0.001 |
| C4 | 20 | 9 | 0.001 |
| C5 | 10 | 4.5 | 0.1 |
| C6 | 20 | 4.5 | 0.1 |
| C7 | 10 | 9 | 0.1 |
| C8 | 20 | 9 | 0.1 |
| C9 | 15 | 6.75 | 0.0505 |
| C10 | 15 | 6.75 | 0.0505 |

TABLE 9

Full Factorial Design in Histidine Buffer
(3 factors at 2 levels with 2 center points)

| Run Order | Buffer (mM) | Sucrose (%) | Polysorbate 80 (%) |
|---|---|---|---|
| H1 | 10 | 4.5 | 0.001 |
| H2 | 20 | 4.5 | 0.001 |
| H3 | 10 | 9 | 0.001 |
| H4 | 20 | 9 | 0.001 |
| H5 | 10 | 4.5 | 0.1 |
| H6 | 20 | 4.5 | 0.1 |
| H7 | 10 | 9 | 0.1 |
| H8 | 20 | 9 | 0.1 |
| H9 | 15 | 6.75 | 0.0505 |
| H10 | 15 | 6.75 | 0.0505 |

To prepare individual formulation, protein solution of 60 mg/ml 1008 in citrate buffer containing 0.001% polysorbate 20/0.73% NaCl at pH 6.25 was used. The protein solution was first buffer exchanged to a vehicle using NAP-25 column. This vehicle contained buffer and sucrose at their target concentrations. The exchanged protein solution was concentrated to a concentration of about 60 mg/ml using Vivaspin 10 kDa MWCO.

Batch amounts of polysorbate 80 and sodium chloride were then added to make the final formulation compositions. The protein concentration in each sample was verified with theoretical extinction coefficient using absorbance measured by UV at 280 nm.

The prepared formulations were then filtered through 0.2 μm PVDF syringe filter to a 4 mL clean clear glass vial. About 100 μL sample was used for initial assay by SEC and IEX, while about 2-2.5 mL samples were stored at 40° C. About 600 μL sample was pulled after storage for 11, 20, and 27 days at 40° C. for analysis by MFI, SEC and IEX.

Based on Study 1 results, a full factorial study containing three factors at two levels with two center points were performed in citrate and histidine buffers respectively, in order to determine the optimum concentration for each selected formulation component. The tested samples were stored at 40° C., and pulled at 0, 1.6, 2.9 and 4 weeks for MFI, SEC and IEX analysis. The results are tabulated in the Tables 10 and 11.

TABLE 10

Stability Results for Citrate Buffered Solutions

| | Time (wk) | | | | | | | |
|---|---|---|---|---|---|---|---|---|
| | 0 | 1.6 | 2.9 | 4 | 0 | 1.6 | 2.9 | 4 |
| | Condition | | | | | | | |
| | 10 mM Citrate/4.5% Sucrose/0.001% PS80) | | | | 20 mM Citrate/4.5% Sucrose/0.001% PS80 | | | |
| 1008 (mg/ml) | 59.1 | | | | 58.7 | | | |
| Particles ≥10 μm #/mL by MFI | — | 61.1 | 91.7 | 36518 | — | 27 | 203 | 51209 |
| Particles ≥25 μm #/mL by MFI | — | 7.64 | 15.29 | 6508 | — | 4 | 27 | 5071 |
| Particles ≥50 μm #/mL by MFI | — | 0 | 0 | 325 | — | 0 | 4 | 61 |
| Total Particles #/mL by MFI | — | 2881 | 7165 | 82439 | — | 627 | 26078 | 577345 |
| SEC (% Initial) | 99.2 | 93.4 | 89.6 | 85.8 | 99.3 | 93.8 | 90.1 | 86.4 |
| IEX (% Initial) | 97.7 | 91.4 | 85.3 | 81.4 | 96.8 | 92.7 | 87.2 | 83.3 |
| | Condition | | | | | | | |
| | 10 mM Citrate/9% Sucrose/0.001% PS80 | | | | 20 mM Citrate/9% Sucrose/0.001% PS80 | | | |
| 1008 (mg/ml) | 54.2 | | | | 53.3 | | | |
| Particles ≥10 μm #/mL by MFI | — | 38 | 57 | 84 | — | 19 | 42 | 126 |

TABLE 10-continued

Stability Results for Citrate Buffered Solutions

| | Time (wk) | | | | | | | |
|---|---|---|---|---|---|---|---|---|
| | 0 | 1.6 | 2.9 | 4 | 0 | 1.6 | 2.9 | 4 |
| Particles ≥25 μm #/mL by MFI | — | 4 | 0 | 8 | — | 8 | 0 | 11 |
| Particles ≥50 μm #/mL by MFI | — | 0 | 0 | 0 | — | 0 | 0 | 0 |
| Total Particles #/mL by MFI | — | 791 | 1838 | 6993 | — | 841 | 1594 | 8472 |
| SEC (% Initial) | 99.2 | 93.5 | 89.7 | 86.2 | 99.5 | 93.4 | 89.9 | 86.5 |
| IEX (% Initial) | 97.5 | 91.1 | 85.3 | 81.4 | 97.4 | 91.8 | 86.3 | 82.6 |

| | Condition | | | | | | | |
|---|---|---|---|---|---|---|---|---|
| | 10 mM Citrate/4.5% Sucrose/0.1% PS80 | | | | 20 mM Citrate/4.5% Sucrose/0.1% PS80 | | | |
| 1008 (mg/ml) | 58.7 | | | | 58.7 | | | |
| Particles ≥10 μm #/mL by MFI | — | 76 | 27 | 31 | — | 34 | 149 | 187 |
| Particles ≥25 μm #/mL by MFI | — | 0 | 4 | 8 | — | 11 | 31 | 31 |
| Particles ≥50 μm #/mL by MFI | — | 0 | 0 | 0 | — | 4 | 0 | 0 |
| Total Particles #/mL by MFI | — | 1104 | 803 | 23839 | — | 860 | 1494 | 31451 |
| SEC (% Initial) | 99.2 | 92.4 | 87.5 | 82.3 | 99.5 | 92.3 | 87.4 | 82.5 |
| IEX (% Initial) | 97.5 | 90.2 | 83.1 | 78.0 | 97.5 | 90.6 | 84.0 | 78.8 |

| | Condition | | | | | | | |
|---|---|---|---|---|---|---|---|---|
| | 10 mM Citrate/9% Sucrose/0.1% PS80 | | | | 20 mM Citrate/9% Sucrose/0.1% PS80 | | | |
| 1008 (mg/ml) | 54.7 | | | | 52.5 | | | |
| Particles ≥10 μm #/mL by MFI | — | 103 | 187 | 164 | — | 88 | 65 | 99 |
| Particles ≥25 μm #/mL by MFI | — | 23 | 42 | 27 | — | 23 | 11 | 19 |
| Particles ≥50 μm #/mL by MFI | — | 0 | 4 | 2 | — | 0 | 4 | 0 |
| Total Particles #/mL by MFI | — | 2538 | 3642 | 4055 | — | 1062 | 1613 | 2117 |
| SEC (% Initial) | 98.9 | 93.2 | 88.5 | 84.0 | 99.4 | 92.8 | 88.3 | 84.0 |
| IEX (% Initial) | 97.2 | 90.9 | 83.8 | 79.1 | 97.1 | 91.3 | 84.3 | 79.7 |

| | Condition | | | | | | | |
|---|---|---|---|---|---|---|---|---|
| | 15 mM Citrate/6.75% Sucrose/0.0505% PS80 | | | | 15 mM Citrate/6.75% Sucrose/0.0505% PS80 | | | |
| 1008 (mg/ml) | 50.8 | | | | 51.3 | | | |
| Particles ≥10 μm #/mL by MFI | | 42 | 54 | 42 | | 31 | 15 | |
| Particles ≥25 μm #/mL by MFI | | 8 | 8 | 0 | | 4 | 4 | |
| Particles ≥50 μm #/mL by MFI | | 0 | 4 | 0 | | 0 | 0 | |
| Total Particles #/mL by MFI | | 439 | 1368 | 1536 | | 1162 | 1727 | |
| SEC (% Initial) | 99.1 | 93.6 | 88.8 | 84.7 | 99.4 | 92.9 | 88.3 | 84.1 |
| IEX (% Initial) | 97.0 | 91.5 | 85.0 | 80.6 | 97.0 | 91.4 | 84.7 | 80.0 |

TABLE 11

Stability Results for Histidine Buffered Solutions

| | Time (week) | | | | | | | |
|---|---|---|---|---|---|---|---|---|
| | 0 | 1.6 | 2.9 | 4 | 0 | 1.6 | 2.9 | 4 |
| | Condition | | | | | | | |
| | 10 mM Histidine/4.5% Sucrose/0.001% PS80 | | | | 20 mM Histidine/4.5% Sucrose/0.001% PS80 | | | |
| 1008 (mg/ml) | 48.8 | | | | 50.6 | | | |
| Particles ≥10 μm #/mL by MFI | — | 26.75 | 152.86 | 596 | | 30.57 | 95.54 | 4265 |
| Particles ≥25 μm #/mL by MFI | — | 15.29 | 11.46 | 76.43 | | 0 | 7.64 | 172 |
| Particles ≥50 μm #/mL by MFI | — | 0 | 0 | 7.64 | | 0 | 0 | 3.82 |
| Total Particles #/mL by MFI | — | 634 | 2927 | 42083 | | 592 | 14204 | 246370 |
| SEC (% Initial) | 99.6 | 93.4 | 89.5 | 85.9 | 99.6 | 93.3 | 89.6 | 86.4 |
| IEX (% Initial) | 96.7 | 91.9 | 86.2 | 82.5 | 96.9 | 91.9 | 86.2 | 82.4 |
| | Condition | | | | | | | |
| | 10 mM Histidine/9% Sucrose/0.001% PS80 | | | | 20 mM Histidine/9% Sucrose/0.001% PS80 | | | |
| 1008 (mg/ml) | 54.8 | | | | 55.6 | | | |
| Particles ≥10 μm #/mL by MFI | | 19.11 | 64.97 | 202.54 | | 15.29 | 103.18 | 149.04 |
| Particles ≥25 μm #/mL by MFI | | 7.64 | 7.64 | 26.75 | | 0 | 15.29 | 15.29 |
| Particles ≥50 μm #/mL by MFI | | 0 | 0 | 0 | | 0 | 11.46 | 3.82 |
| Total Particles #/mL by MFI | | 684 | 2538 | 7505 | | 806 | 3565 | 8102 |
| SEC (% Initial) | 99.7 | 92.8 | 88.9 | 85.5 | 98.8 | 93.4 | 89.5 | 85.9 |
| IEX (% Initial) | 97.0 | 90.78 | 84.8 | 81.1 | 97.1 | 90.6 | 84.4 | 80.3 |
| | Condition | | | | | | | |
| | 10 mM Histidine/4.5% Sucrose/0.1% PS80 | | | | 20 mM Histidine/4.5% Sucrose/0.1% PS80 | | | |
| 1008 (mg/ml) | 48.8 | | | | 49.8 | | | |
| Particles ≥10 μm #/mL by MFI | — | 68.8 | 76.4 | 126 | | 34 | 42 | 54 |
| Particles ≥25 μm #/mL by MFI | — | 15.3 | 3.82 | 19.1 | | 0 | 4 | 8 |
| Particles ≥50 μm #/mL by MFI | — | 7.64 | 0 | 0 | | 0 | 4 | 0 |
| Total Particles #/mL by MFI | — | 753 | 2033 | 2782 | | 1311 | 1704 | 1724 |
| SEC (% Initial) | 99.7 | 92.7 | 87.6 | 83.9 | 99.7 | 92.7 | 88.0 | 83.8 |
| IEX (% Initial) | 96.9 | 90.7 | 84.5 | 78.7 | 97.0 | 91.0 | 84.4 | 78.1 |
| | Condition | | | | | | | |
| | 10 mM Histidine/9% Sucrose/0.1% PS80 | | | | 20 mM Histidine/9% Sucrose/0.1% PS80 | | | |
| 1008 (mg/ml) | 54.1 | | | | 54.6 | | | |
| Particles ≥10 μm #/mL by MFI | | 22.93 | 42.04 | 68.79 | | 64.97 | 72.61 | 80.25 |
| Particles ≥25 μm #/mL by MFI | | 3.82 | 3.82 | 0 | | 0 | 7.64 | 3.82 |
| Particles ≥50 μm #/mL by MFI | | 0 | 0 | 0 | | 0 | 0 | 3.82 |
| Total Particles #/mL by MFI | | 783 | 1330 | 6111 | | 1716 | 2469 | 3844 |
| SEC (% Initial) | 99.3 | 92.8 | 88.2 | 84.0 | 99.7 | 92.7 | 87.6 | 83.3 |
| IEX (% Initial) | 97.0 | 90.5 | 83.4 | 78.7 | 96.8 | 90.9 | 83.3 | 78.3 |

TABLE 11-continued

Stability Results for Histidine Buffered Solutions

|  | Time (week) | | | | | | |
|---|---|---|---|---|---|---|---|
|  | 0 | 1.6 | 2.9 | 4 | 0 | 1.6 | 2.9 | 4 |
|  | Condition | | | | | | | |
|  | 15 mM Histidine/6.75% Sucrose/0.0505% PS80 | | | | 15 mM Histidine/6.75% Sucrose/0.0505% PS80 | | | |
| 1008 (mg/ml) | 50.3 | | | | 49.6 | | | |
| Particles ≥10 μm #/mL by MFI | | 19 | 46 | 172 | | 31 | 80 | 114 |
| Particles ≥25 μm #/mL by MFI | | 0 | 0 | 19 | | 7.6 | 15.3 | 22.9 |
| Particles ≥50 μm #/mL by MFI | | 0 | 0 | 0 | | 0 | 7.6 | 3.8 |
| Total Particles #/mL by MFI | | 1005 | 1788 | 4242 | | 760 | 1823 | 3053 |
| SEC (% Initial) | 99.3 | 92.9 | 87.9 | 84.2 | 99.6 | 92.5 | 87.7 | 83.9 |
| IEX (% Initial) | 97.1 | 90.9 | 84.3 | 79.6 | 96.9 | 91.0 | 84.6 | 79.8 |

The experimental data were analyzed by Minitab. For SEC results in citrate buffer, surfactant was the major factor influencing the protein aggregation, while sucrose, interaction between sucrose and polysorbate 80, and buffer strength played less significant roles. Higher sucrose concentration and lower polysorbate 80 concentration favored the protein stability. The protein stability affected aggregation slightly and higher citrate buffer strength promoted slightly better protein stability.

For MFI results in citrate buffer, factors of sucrose and polysorbate 80 as well as interaction of sucrose and polysorbate 80 played equally significant roles in particulates formation. High sucrose and high polysorbate 80 suppressed particulates formation significantly, while buffer strength in the 10-20 mM range slightly affect the particulate formation, lower buffer strength was preferred.

The results by Minitab analysis of histidine buffer solutions showed the surfactant, polysorbate 80, was the major factor influencing the protein aggregation, while interaction between buffer strength and polysorbate 80, as well as sucrose, played less significant roles. Less polysorbate 80 favored the protein stability. Buffer strength and sucrose concentration did not appear to affect protein aggregation.

For MFI results in histidine buffer, polysorbate 80, sucrose, and interaction of sucrose and polysorbate 80 played significant roles in particulates formation. High sucrose and low polysorbate 80, and low buffer strength were preferred to suppress the particulates formation.

pH Optimization

Effects of pH on the aggregation behavior of 1008 were studied under six pH conditions (5.0, 6.0, 6.25, 6.50, 6.75 and 7.0) in 15 mM citrate buffer containing 0.1% NaCl, 6.75% sucrose and 0.05% PS80. 1008 drug substance was first exchanged into the vehicles (without PS80) of different pH using Illustra NAP-10 column (GE Healthcare). The column was first equilibrated with 15 mL of citrate buffer. Then 1 mL of 1008 DS was loaded onto the column. After the DS solution completed moved into the column, the column was washed with 2 mL of the same citrate buffer used to equilibrate the column. Collect the 2 mL solution eluted from the column in a Vivaspin 2 concentrator (10KD MWCO, GE Healthcare). The 2 mL eluted solution was then concentrated to about 1 mL using a Beckman GS-15R centrifuge at 9384 ×g and 4° C. The concentration of protein was then measured with a NanoDrop 1000 spectrophotometer. The final 1008 concentration for this study was determined to be about 70 mg/ml. PS80 was spiked into the formulations to a final target concentration of 0.05%. The kinetic turbidity assay was conducted using a PerkinElmer Lambda 35 spectrophotometer with a two-position cell holder and a water batch for temperature regulation. In a Starna submicro volume quartz cell (Starna Scientific Ltd., England) with 1 cm path-length, 250 μL of 1008 formulation or the corresponding vehicle was added. The cells were placed into the cell holder that was preheated to 55° C. Change of OD350 in the 1008 formulation was monitored for 120 minutes. The OD350 data obtained for formulations of different pH was then plotted against time for comparison.

Using the turbidity-based kinetic assay, effects of pH on the aggregation behavior of 1008 were studied with the formulations from pH 5.0 to 7.0 containing about 70 mg/ml 1008. For the turbidity assay, a sharp increase in $OD_{350}$ was associated with the major aggregation events of the protein. Thus, the difference in the incubation time required for $OD_{350}$ of each formulation to increase could reflect the different physical stability of the protein in the formulations. As shown in FIG. 1, 1008 appeared to be the most stable at pH 6.75 under the tested formulation conditions, as it had the longest incubation time before the sharp increase of $OD_{350}$. Repeated experiments with similar results confirmed that the tested formulation was most stable at pH 6.75.

Study 3

Effects of Excipients and High Active Concentrations

A half factorial study (Table 12) was performed to investigate the effects of the major formulation conditions including concentrations of protein (60-120 mg/ml), sucrose (4.5-9.0%), citrate buffer (10 to 20 mM) and polysorbate 80 (0.01-0.1%).

TABLE 12

Study design for Study 3

| Run Order | Center Point | Blocks | 1008 (mg/ml) | Sucrose (w/w %) | Buffer (mM) | Polysorbate 80 (%) |
|---|---|---|---|---|---|---|
| 1 | 1 | 1 | 60 | 4.5 | 10 | 0.01 |
| 2 | 1 | 1 | 120 | 4.5 | 10 | 0.1 |
| 3 | 1 | 1 | 60 | 9 | 10 | 0.1 |
| 4 | 1 | 1 | 120 | 9 | 10 | 0.01 |

TABLE 12-continued

Study design for Study 3

| Run Order | Center Point | Blocks | 1008 (mg/ml) | Sucrose (w/w %) | Buffer (mM) | Polysorbate 80 (%) |
|---|---|---|---|---|---|---|
| 5 | 1 | 1 | 60 | 4.5 | 20 | 0.1 |
| 6 | 1 | 1 | 120 | 4.5 | 20 | 0.01 |
| 7 | 1 | 1 | 60 | 9 | 20 | 0.01 |
| 8 | 1 | 1 | 120 | 9 | 20 | 0.1 |
| 9 | 0 | 1 | 90 | 6.75 | 15 | 0.055 |
| 10 | 0 | 1 | 90 | 6.75 | 15 | 0.055 |

To prepare the above formulations, a 20% citrate buffer at pH 6.5 and a 30% sucrose stock solution in 20 mM citrate buffer at pH 6.5 were first prepared. Then the citrate buffer, sucrose stock and water for injection were mixed at appropriate ratios to generate five buffers with PS80, which were 4.5% sucrose in 10 mM citrate, 9% sucrose in 10 mM citrate, 4.5% sucrose in 20 mM citrate, 9% sucrose in 20 mM citrate and 6.75% sucrose in 15 mM citrate. 1008 DS were subsequently exchanged into these five buffers using Illustra NAP-25 column (GE Healthcare) followed by concentrating with Vivaspin 6 concentrator (5 KD MWCO, GE Healthcare) at 8000× at 5° C. The protein concentrations in each sample were determined with a NanoDrop 2000 spectrophotometer during centrifugation. For the samples in the first four buffers, when 1008 concentration reached ~70 mg/ml, part of the sample was removed from the concentrator and used to prepared formulations (#1, 3, 5 and 7 in Table 12) with 60 mg/ml API by adding appropriate amount of corresponding buffer and spiking in 10% PS80. The rest of the samples were concentrated further to above 130 mg/ml and then added buffer and 10% PS80 to obtain the final formulations (#2, 4, 6 and 8 in Table 12). Formulations #9 and 10 in Table 12 were prepared by concentrating the 1008 samples exchanged into buffer #5 to about 108 mg/ml and then mixed with buffer and 10% PS80 to reach the final formulation concentrations. The pH values of all the final formulations were measure and adjusted to 6.5.

A turbidity assay modified from the one described above was used as the analytical tool for evaluation. In this modified turbidity assay, a 12-cell position Cary 100 UV-Vis spectrophotometer was used. The cuvettes used in this assay were 1 mm quartz cuvettes with stoppers. In each cuvette, 300 μL of sample was added for the test. The optical density change at 360 nm was monitored for the formulations incubated at 55° C.

Effects of Excipients and High Active Concentrations

Figure 2A:
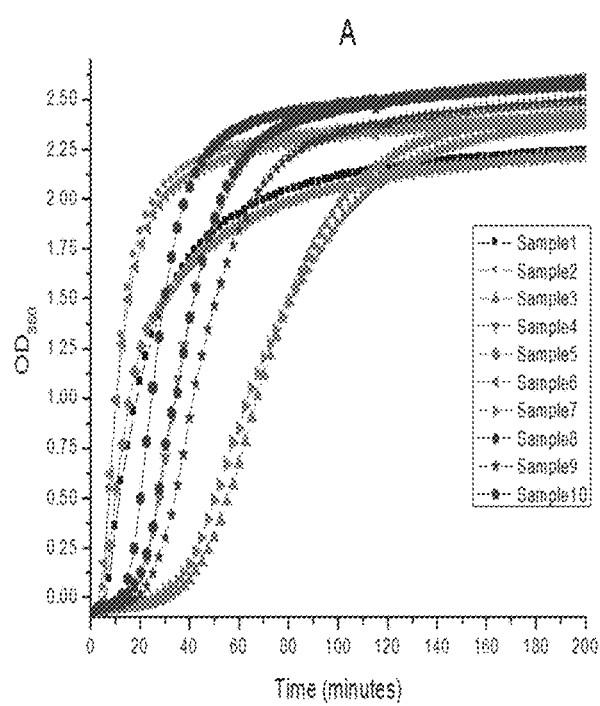
FIG. 2A and FIG. 2B show a turbidity assay monitoring changes in $OD_{360}$ for different 1008 formulations incubated at 55° C. for 180 mins (FIG. 2A). $OD_{360}$ curves obtained in 60 min are expanded and shown in (FIG. 2B). The sample numbers in FIGS. 2A and 2B correspond to the formulation number in Table 13.
Figure 2B:
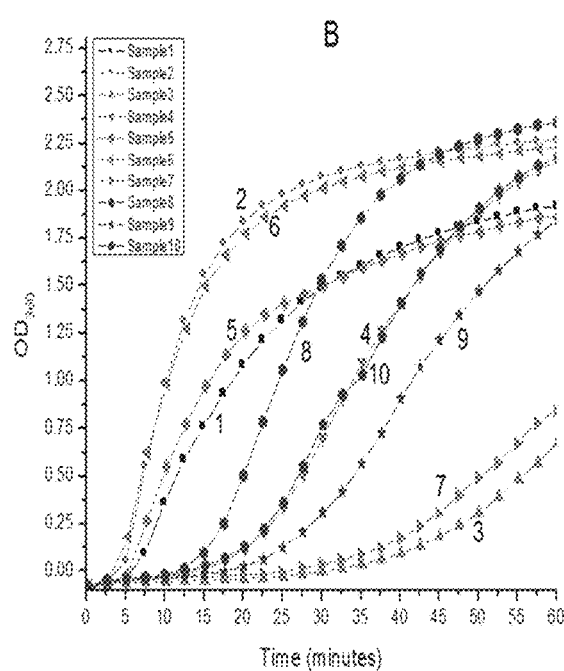

The measured 1008 concentrations and final pH of all the formulations for Study 3 are summarized in Table 13. Formulations with low, medium and high 1008 concentrations (Table 4.3.1.-1) with different sucrose, PS80 concentrations and buffer strength were incubated at 55° C. and changes in $OD_{360}$ were monitored. As shown in FIG. 2, different aggregation propensity was observed for the formulations. The two formulations almost aggregated immediately when incubation started were the formulations 2 and 6, which contained the relatively higher 1008 concentration (~120 mg/ml) and lower sucrose concentration (4.5%). On the other hand, formulations 3 and 7, containing the relatively lower 1008 concentration (~60 mg/ml) and higher sucrose concentration (9%), aggregated slower than other formulations. The aggregation propensity of other combinations of medium 1008 and sucrose concentrations fell in between the above two groups.

TABLE 13

Final formulation conditions for Study 3

| Formulation # | Excipient concentrations | Final 1008 Concentration (mg/ml) | Final pH |
|---|---|---|---|
| 1 | 10 mM citrate/4.5% sucrose/0.01% PS80 | 58.223 (lower) | 6.56 |
| 2 | 10 mM citrate/4.5% sucrose/0.1% PS80 | 113.554 (higher) | 6.53 |
| 3 | 10 mM citrate/9% sucrose/0.1% PS80 | 59.034 (lower) | 6.55 |
| 4 | 10 mM citrate/9% sucrose/0.01% PS80 | 117.489 (higher) | 6.48 |
| 5 | 20 mM citrate/4.5% sucrose/0.1% PS80 | 58.910 (lower) | 6.53 |
| 6 | 20 mM citrate/4.5% sucrose/0.01% PS80 | 116.712 (higher) | 6.50 |
| 7 | 20 mM citrate/9% sucrose/0.01% PS80 | 57.431 (lower) | 6.47 |
| 8 | 20 mM citrate/9% sucrose/0.1% PS80 | 116.466 (higher) | 6.45 |
| 9 | 15 mM citrate/6.75% sucrose/0.055% PS80 | 87.555 (medium) | 6.48 |
| 10 | 15 mM citrate/6.75% sucrose/0.055% PS80 | 87.769 (medium) | 6.49 |

Using the time for $OD_{360}$ of each formulation to reach 0.25 as the criteria, the effects of different formulation factors were compared. The results suggested that sucrose had the largest impact on the aggregation of 1008, followed by API concentration. The effects of sucrose and API concentrations were opposite, indicating higher sucrose and lower API concentrations were preferred for better formulation stability. Other two factors, buffer strength and PS80 showed less effect.

Study 4

Further Study on Active and Sucrose Concentrations

Based on the results from above Study 3, Study 4 was conducted to further investigate the effects of protein concentration (60-120 mg/ml) and sucrose concentration (with a narrower range of 6 to 9%) in 15 mM citrate buffer containing 0.05% PS 80 at pH 6.50. The study design is shown in the table below.

TABLE 14

Study Design for Study 4

| Run Order | Center Point | Blocks | 1008 (mg/ml) | Sucrose (w/w %) |
|---|---|---|---|---|
| 1 | 1 | 1 | 60 | 6 |
| 2 | 1 | 1 | 120 | 6 |
| 3 | 1 | 1 | 60 | 9 |
| 4 | 1 | 1 | 120 | 9 |
| 5 | −1 | 1 | 47.6 | 7.5 |
| 6 | −1 | 1 | 132.4 | 7.5 |
| 7 | −1 | 1 | 90 | 5.4 |
| 8 | −1 | 1 | 90 | 9.6 |
| 9 | 0 | 1 | 90 | 7.5 |
| 10 | 0 | 1 | 90 | 7.5 |
| 11 | 0 | 1 | 90 | 7.5 |
| 12 | 0 | 1 | 90 | 7.5 |

To prepare the formulations, about 80 g of 1008 drug substance was loaded into a TFF system and then buffer exchange was conducted with 15 mM citrate buffer containing 6% sucrose at about 5 times the volume of the drug substance. After buffer exchange, the volume of the protein solution was reduced to about half of the initial volume using the TFF system. About 44 g of concentrated 1008 solution was recovered and the protein concentrated was about 112 mg/ml measured by the NanoDrop 2000 spectrophotometer. The concentrated 1008 solution was then used to prepare formulations #1, 3, 5, 7-12 by mixing with appropriate amount of 10% PS80 and 15 mM citrate buffers containing 0, 6% and/or 40% sucrose to obtain the corresponding final API, sucrose and PS80 concentrations in each of these formulations. The rest of the 1008 solution was further concentrated to about 132 mg/ml to prepare formulations #2 and 4 in the same fashion. Lastly, formulation #6 was prepared by concentrating 1008 solution to about 171 mg/ml and the concentrations of protein, sucrose and PS80 were adjusted with 10% PS80 and 15 mM citrate buffers containing 0, 6% and/or 40% sucrose. The final concentration of 1008 in each formulation was determined with the NanoDrop 2000 spectrophotometer and the pH was adjusted to 6.5.

The samples were analyzed using the turbidity assay described above. Eight selected formulations (#1-4 and #7-10) were also stored in a 40° C. exploratory incubator for 6 weeks and analyzed with MIF, IEX and SEC methods at different time points.

Twelve formulations, as listed in Table 15 were investigated.

TABLE 15

Final formulation conditions and $T_m$ from the turbidity assay for Study 4

| Formulation # | Sucrose Conc | Final 1008 (mg/ml) | Final pH | $T_m$ (minutes) |
|---|---|---|---|---|
| 1 | 6% | 61.6 | 6.49 | 62.0 |
| 2 | 6% | 122.8 | 6.49 | 27.4 |
| 3 | 9% | 60.0 | 6.50 | 86.3 |
| 4 | 9% | 119.0 | 6.51 | 34.2 |
| 5 | 7.5% | 47.7 | 6.50 | 97.0 |
| 6 | 7.5% | 134.5 | 6.50 | 24.2 |
| 7 | 5.38% | 94.6 | 6.50 | 33.1 |
| 8 | 9.62% | 86.2 | 6.50 | 49.4 |
| 9 | 7.5% | 91.7 | 6.50 | 41.2 |
| 10 | 7.5% | 89.5 | 6.50 | 44.5 |
| 11 | 7.5% | 88.4 | 6.48 | 38.6 |
| 12 | 7.5% | 90.1 | 6.52 | 40.0 |

Figure 3:
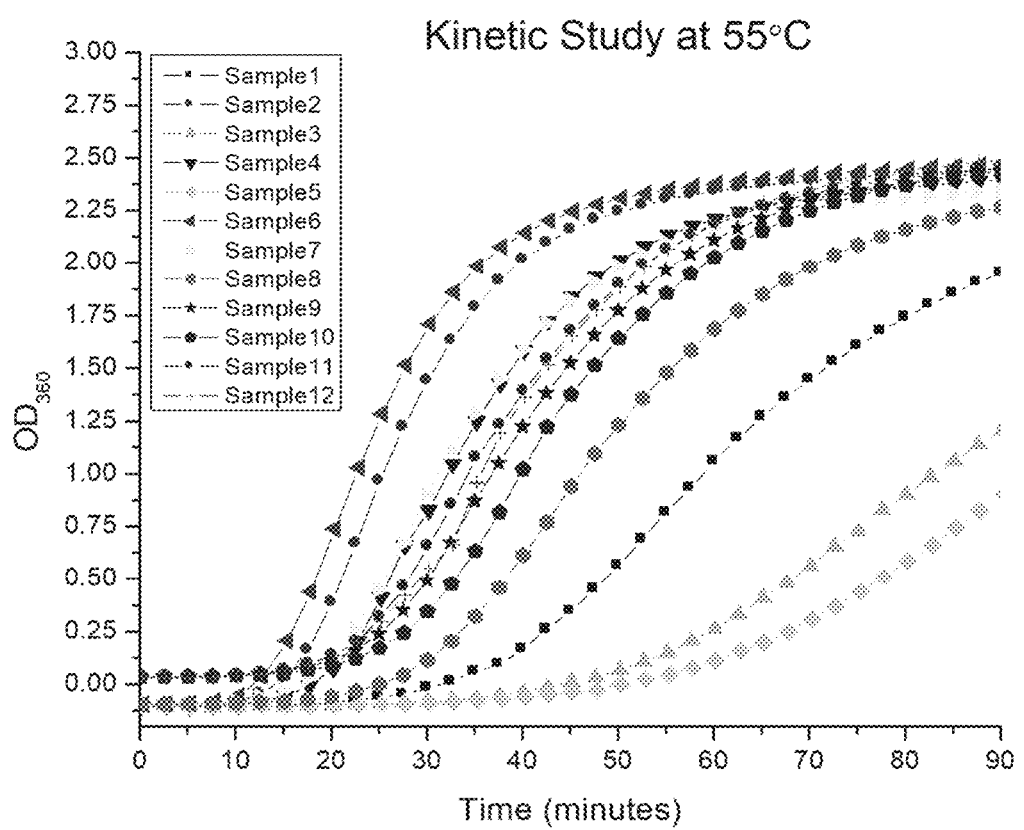
FIG. 3 shows a turbidity assay with data collected between zero to 90 minutes for simplicity. The entire experiment was 180 minutes. Changes in $OD_{360}$ were monitored for different 1008 formulations incubated at 55° C. The sample numbers in the figure correspond to the formulation numbers in Table 15.

The turbidity assay at 55° C. was used to monitor the aggregation of the formulations. As shown in FIG. 3, different degrees of aggregation were shown by the formulations under the same thermal stress. Formulations with the relatively higher 1008 and low sucrose concentrations (such as formulations #2 and 6 in Table 15) were the ones that aggregated rapidly upon incubation. The formulations with relatively lower 1008 and high sucrose concentrations (formulations #3 and 5 in Table 15) aggregated slower than all the rest of the formulations. The curves obtained from the turbidity assay for the various formulations were fitted to a sigmoidal function. The incubation time corresponds to the middle of a transition was recorded as $T_m$ (transition midpoint time) for each formulation. The results are listed in Table 15. $T_m$ values against sucrose and 1008 concentrations showed the opposite effects of sucrose and 1008 concentrations on the protein aggregation.

Besides studies using the turbidity assay at 55° C., stability of eight selected formulations at 40° C. were also monitored by MFI, SEC and IEX over 6 weeks. Formulations and results are listed in Tables 16 to 23. In agreement with turbidity assay, MFI results showed that formulations with high 1008 concentration (~120 mg/ml) formed more particles especially particles greater than 25 μm, in comparison with formulations with lower API concentrations.

Figure 4:
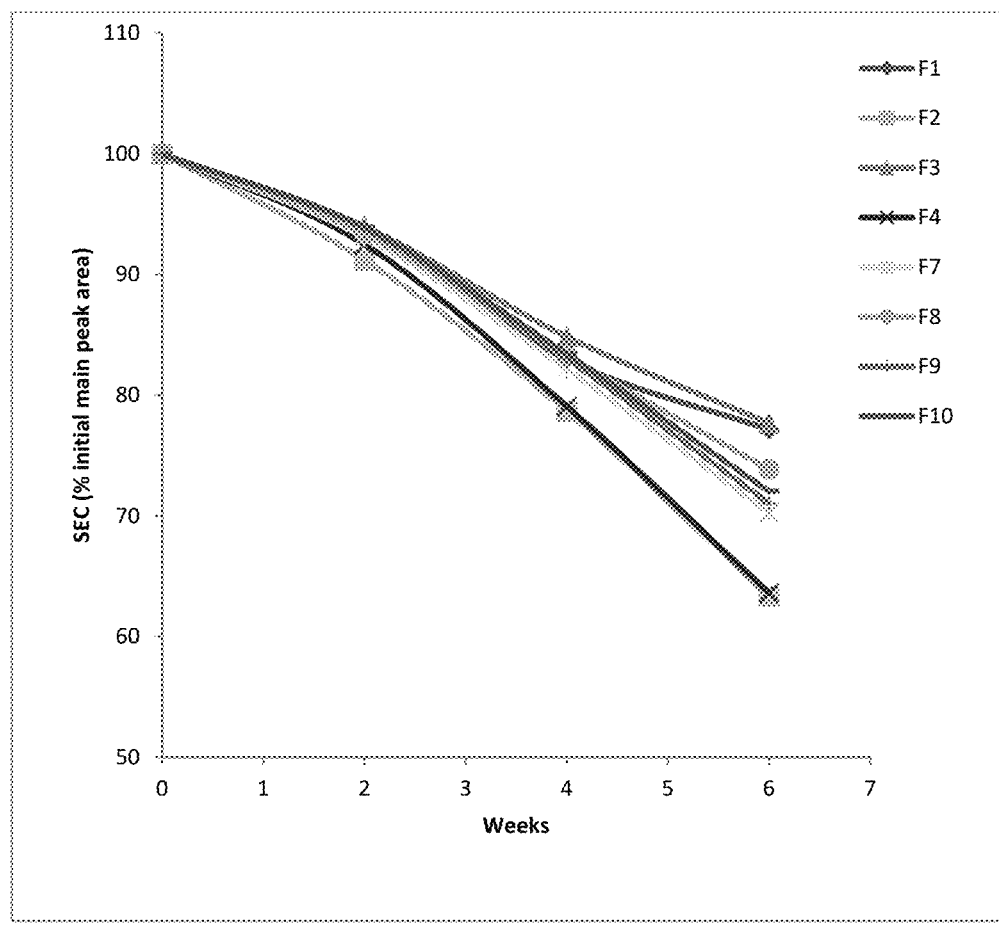
FIG. 4 is a graph showing SEC results for the main peak in the eight selected formulations during the 6 weeks storage at 40° C.

The MFI results didn't show clear effects of sucrose concentration for the formulations with similar amount of 1008 (formulations #7 to 10). As shown in FIG. 4, after 6-week storage at 40° C., the two formulations (#2 and 4) with the high 1008 concentration degraded the most, which the formulations with ~60 mg/ml 1008 degraded less than all other formulations. As for formulations with ~90 mg/ml 1008, slightly less degradation was observed at higher sucrose concentration (formulations #8) than at the lower sucrose concentration (formulation #7). IEX results showed the same trend as the SEC.

TABLE 16

Results of the accelerated stability study at 40° C. for formulation #1 from Study 4

Formulation conditions
F1: 61.6 mg/ml 1008 in 15 mM citrate, 6% sucrose, 0.05% PS80, pH 6.5

| Particulates by MFI | Initial | 2 week | 4 week | 6 week |
|---|---|---|---|---|
| ≥10 μm, <100 μm (#/mL) | 42 | 18 | 107 | 26 |
| ≥25 μm, <100 μm (#/mL) | 6 | 2 | 4 | 4 |
| ≥50 μm, <100 μm (#/mL) | 0 | 0 | 0 | 0 |
| ≥2 μm, <100 μm (#/mL) | 1076 | 656 | 12911 | 2076 |
| SEC (% initial) | 99.9 | 93.6 | 83.0 | 77.1 |
| IEX (% initial) | 97.7 | 92.8 | 83.2 | 76.8 |

TABLE 17

Results of the accelerated stability study at 40° C. for formulation #2 from Study 4

Formulation conditions
F2: 122.8 mg/ml 1008 in 15 mM citrate, 6% sucrose, 0.05% PS80, pH 6.5

| Particulates by MFI | Initial | 2 week | 4 week | 6 week |
|---|---|---|---|---|
| ≥10 μm, <100 μm (#/mL) | 36 | 8 | 16 | 32 |
| ≥25 μm, <100 μm (#/mL) | 8 | 2 | 2 | 2 |
| ≥50 μm, <100 μm (#/mL) | 2 | 2 | 0 | 0 |
| ≥2 μm, <100 μm (#/mL) | 1267 | 994 | 235 | 4856 |
| SEC (% initial) | 100.0 | 91.2 | 78.7 | 63.3 |
| IEX (% initial) | 97.8 | 91.0 | 79.1 | 69.3 |

TABLE 18

Results of the accelerated stability study at 40° C. for formulation #3 from Study 4

Formulation conditions
F3: 60.0 mg/ml 1008 in 15 mM citrate, 9% sucrose, 0.05% PS80, pH 6.5

| Particulates by MFI | Initial | 2 week | 4 week | 6 week |
|---|---|---|---|---|
| ≥10 μm, <100 μm (#/mL) | 10 | 22 | 16 | 28 |
| ≥25 μm, <100 μm (#/mL) | 0 | 0 | 0 | 2 |
| ≥50 μm, <100 μm (#/mL) | 0 | 0 | 0 | 0 |
| ≥2 μm, <100 μm (#/mL) | 959 | 782 | 897 | 2428 |
| SEC (% initial) | 100.0 | 94.0 | 84.8 | 77.7 |
| IEX (% initial) | 97.8 | 93.1 | 84.4 | 76.9 |

TABLE 19

Results of the accelerated stability study at 40° C. for formulation #4 from Study 4

Formulation conditions
F4: 119.0 mg/ml 1008 in 15 mM citrate, 9% sucrose, 0.05% PS80, pH 6.5
Time

| Particulates by MFI | Initial | 2 week | 4 week | 6 week |
|---|---|---|---|---|
| ≥10 μm, <100 μm (#/mL) | 12 | 24 | 4 | 16 |
| ≥25 μm, <100 μm (#/mL) | 0 | 0 | 0 | 4 |
| ≥50 μm, <100 μm (#/mL) | 0 | 0 | 0 | 2 |
| ≥2 μm, <100 μm (#/mL) | 366 | 581 | 384 | 2659 |
| SEC (% initial) | 100.0 | 92.5 | 79.1 | 63.6 |
| IEX (% initial) | 97.8 | 92.2 | 81.3 | 69.1 |

TABLE 20

Results of the accelerated stability study at 40° C. for formulation #7 from Study 4

Formulation conditions
F7: 94.6 mg/ml 1008 in 15 mM citrate, 5.4% sucrose, 0.05% PS80, pH 6.5

| Particulates (MFI) | Initial | 2 week | 4 week | 6 week |
|---|---|---|---|---|
| ≥10 μm, <100 μm (#/mL) | 14 | 20 | 6 | 6 |
| ≥25 μm, <100 μm (#/mL) | 0 | 0 | 0 | 0 |
| ≥50 μm, <100 μm (#/mL) | 0 | 0 | 0 | 0 |
| ≥2 μm, <100 μm (#/mL) | 626 | 1647 | 843 | 2896 |
| SEC (% initial) | 100.0 | 93.1 | 82.2 | 70.3 |
| IEX (% initial) | 97.9 | 92.5 | 82.6 | 71.5 |

TABLE 21

Results of the accelerated stability study at 40° C. for formulation #8 from Study 4

Formulation conditions
F8: 86.2 mg/ml 1008 in 15 mM citrate, 9.6% sucrose, 0.05% PS80, pH 6.5
Time

| Particulates by MFI | Initial | 2 week | 4 week | 6 week |
|---|---|---|---|---|
| ≥10 μm, <100 μm (#/mL) | 4 | 18 | 8 | 8 |
| ≥25 μm, <100 μm (#/mL) | 0 | 0 | 0 | 0 |
| ≥50 μm, <100 μm (#/mL) | 0 | 0 | 0 | 0 |
| ≥2 μm, <100 μm (#/mL) | 533 | 1810 | 1281 | 2162 |
| SEC (% initial) | 100.0 | 93.3 | 83.2 | 73.8 |
| IEX (% initial) | 97.8 | 93.1 | 83.6 | 73.9 |

TABLE 22

Results of the accelerated stability study at 40° C. for formulation #9 from Study 4

Formulation conditions
F9: 91.7 mg/ml 1008 in 15 mM citrate, 7.5% sucrose, 0.05% PS80, pH 6.5
Time

| Particulates by MFI | Initial | 2 week | 4 week | 6 week |
|---|---|---|---|---|
| ≥10 μm, <100 μm (#/mL) | 6 | 20 | 6 | 28 |
| ≥25 μm, <100 μm (#/mL) | 0 | 0 | 2 | 0 |
| ≥50 μm, <100 μm (#/mL) | 0 | 0 | 0 | 0 |
| ≥2 μm, <100 μm (#/mL) | 678 | 682 | 1068 | 4003 |
| SEC (% initial) | 100.0 | 93.8 | 83.0 | 71.0 |
| IEX (% initial) | 97.8 | 93.2 | 83.7 | 72.2 |

TABLE 23

Results of the accelerated stability study at 40° C. for formulation #10 from Study 4

Formulation conditions
F10: 89.5 mg/ml 1008 in 15 mM citrate, 7.5% sucrose, 0.05% PS80, pH 6.5
Time

| Particulates by MFI | Initial | 2 week | 4 week | 6 week |
|---|---|---|---|---|
| ≥10 μm, <100 μm (#/mL) | 18 | 10 | 22 | 44 |
| ≥25 μm, <100 μm (#/mL) | 0 | 2 | 4 | 0 |
| ≥50 μm, <100 μm (#/mL) | 0 | 0 | 0 | 0 |
| ≥2 μm, <100 μm (#/mL) | 352 | 638 | 1068 | 2536 |
| SEC (% initial) | 100.0 | 93.9 | 83.4 | 72.0 |
| IEX (% initial) | 97.9 | 93.5 | 83.7 | 72.9 |

Example 3

Exploratory Stability Studies

Control Formulation

Exploratory stability was performed for a formulation of 60 mg/ml 1008 solution in 20 mM citrate, 0.001% PS20 at pH 6.25 as a control. The control formulation was filtered through 0.2 um syringe filter and stored at 40° C., ambient room temperature, and refrigerator. The samples were pulled at 0, 2 and 5 weeks for 40° C. samples, and 26 weeks for samples stored at ambient room temperature and refrigerator. The selected stability samples were tested for pH, osmolality, content by A280, SEC, IEX CGE and ELISA. The results are shown in Table 24.

TABLE 24

Exploratory Stability results for Control formulation (60 mg/ml 1008 in 20 mM citrate, 0.001% PS20 at pH 6.25)

| | | Temp | | |
|---|---|---|---|---|
| | | 40° C. | | RT | 2-8° C. |
| Time (week) | 0 | 2 | 5 | 26 | 26 |
| Concentration by A280 (mg/ml) | na | 62 | 61* | na | na |
| pH | na | 6.297 | 6.333 | na | na |
| Osmolality | na | 312 | 310 | na | na |
| SEC (% Initial) | 100 | 90.6 | 75.6 | 88.8 | 99.4 |
| IEX (% Initial) | 100 | 91.3 | 70.9 | 88.5 | 99.3 |
| CGE | na | 99.3 | 98.3 | na | na |
| ELISA | na | na | 1.0 | na | na |

*The sample was visually observed as cloudy with white precipitation.

Another study on the control formulation was performed for 60 mg/ml 1008 solution in 20 mM citrate, 0.001% PS20 and 0.73% NaCl at pH6.25. The formulation was filtered through 0.2 μm syringe filter and stored in 40° C. The samples were pulled at 1, 2, 3, and 4 weeks for MFI analysis. The results are shown in Table 25.

TABLE 25

Stability results for POC formulation at 40° C. (60 mg/ml 1008 in 20 mM citrate, 0.001% PS20 at pH 6.25)

| Time (week) | 0 | 1 | 2 | 3 | 4 |
|---|---|---|---|---|---|
| ≥10 um by MFI (#/mL) | na | 172 | 894 | 2946 | 3183 |
| ≥25 um by MFI (#/mL) | na | 23 | 157 | 539 | 1189 |

TABLE 25-continued

Stability results for POC formulation at 40° C.
(60 mg/ml 1008 in 20 mM citrate, 0.001% PS20 at pH 6.25)

| Time (week) | 0 | 1 | 2 | 3 | 4 |
|---|---|---|---|---|---|
| ≥50 um by MFI (#/mL) | na | 4 | 19 | 92 | 248 |
| Total particles by MFI (#/mL) | na | 2381 | 8954 | 29716 | 17705 |

Exploratory Stability Study for 60 mg/ml 1008 with 9% Sucrose and 0.5% Polysorbate 80

Exploratory stability was performed for 60 mg/ml 1008 formulation containing 9% sucrose and 0.5% PS80. The formulation was filtered through 0.2 μm syringe filter and stored at 40° C. The samples were pulled at 1.6, 2.9 and 4 weeks and analyzed by MFI, SEC and IEX. The results are tabulated in Table 26.

TABLE 26

Stability results for 60 mg/ml 1008 formulation
at 40° C. (60 mg/ml 1008 in 20 mM citrate,
9% sucrose and 0.5% PS80 at pH 6.25)

| Time (week) | 0 | 1.6 | 2.9 | 4 |
|---|---|---|---|---|
| ≥10 um by MFI (#/mL) | — | 12 | 80 | 130 |
| ≥25 um by MFI (#/mL) | — | 4 | 12 | 12 |
| ≥50 um by MFI (#/mL) | — | 0 | 4 | 0 |
| Total particles by MFI (#/mL) | — | 688 | 2900 | 4876 |
| SEC (% Initial) | 98.4 | 93.3 | 88.6 | 84.1 |
| IEX (% Initial) | 97.0 | 91.3 | 83.9 | 78.9 |

Pilot Stability Study for 60 mg/ml 1008, 9% sucrose, 20 mM citrate, 0.1% PS80 at pH6.25

Real time stability study of 60 mg/ml 1008 solution was conducted for the formulation containing 9% sucrose, 20 mM citrate, 0.1% PS80 at pH6.25 as shown in Table 27. The stability samples were stored at 2-8° C., 25° C., 40° C. and light cabinet (LC); they also went through three cycles of freeze-thaw (FT). The samples were pulled according to the schedule shown in Table 28, and analyzed by various analytical methods such as pH, osmolality, MFI, content, SEC, IEX, CGE and potency.

TABLE 27

Composition of Pilot Stability Formulation

| Component | Concentration (W/V %) |
|---|---|
| 1008 | 6 |
| Citric Acid, anhydrous | 0.012 |
| Trisodium citrate (dihydrate) | 0.57 |
| Sucrose | 9 |
| Polysorbate 80 | 0.1 |
| Hydrochloric acid or Sodium hydroxide | pH 6.25 |
| Water for injection | qs 100 |

TABLE 28

Storage Condition and Pull Schedule for Pilot Stability Study

| Condition | Pull |
|---|---|
| 2-8° C. (refrigerator) | 0, 4, 6.9, 8, 12, and 26 weeks |
| 25° C. | 2, 4, 6.9, 8, 12, and 26 weeks |
| 40° C. | 1.1, 2, and 4 weeks |
| Light cabinet (LC) | 6 weeks |
| Freeze Thaw (FT) | 3 cycles |

In the early stage, real time stability study of 60 mg/ml 1008 solution was initiated. The formulation contained 9% sucrose, 20 mM citrate, 0.1% PS80 at pH6.25 as shown in Table 29. The samples were stored at 2-8° C., 25° C., 40° C. and light cabinet (LC); they also went through three cycles of freeze-thaw (FT). The samples were pulled according to the schedule shown in Table 30, and analyzed by various analytical methods. The stability results are tabulated in Tables 31-33.

TABLE 29

Composition of Pilot Stability Formulation
60 mg/ml 1008 (1008) Solution

| Component | Concentration (W/V %) |
|---|---|
| 1008 | 6 |
| Citric Acid, anhydrous | 0.012 |
| Trisodium citrate (dihydrate) | 0.57 |
| Sucrose | 9 |
| Polysorbate 80 | 0.1 |
| Hydrochloric acid or Sodium hydroxide | pH 6.25 |
| Water for injection | qs 100 |

TABLE 30

Storage Condition and Pull Schedule for Pilot Stability Study

| Condition | Pull |
|---|---|
| 2-8° C. (refrigerator) | 0, 4, 6.9, 8, 12, and 26 weeks |
| 25° C. | 2, 4, 6.9, 8, 12, and 26 weeks |
| 40° C. | 1.1, 2, and 4 weeks |
| Light cabinet (LC) | 6 weeks |
| Freeze Thaw (FT) | 3 cycles |

TABLE 31

Results (Part 1/3) of Pilot Stability Study
for 6% 1008, 9% sucrose, 20 mM citrate, 0.1% PS80 at pH 6.25

| Temperature | 2-8 C. | | | | | |
|---|---|---|---|---|---|---|
| Time (wk) | 0 | 4 | 6.9 | 8 | 12 | 26 |
| ≥10 um by MFI (#/mL) | 31 | 57 | 134 | 8 | 19 | 42 |
| ≥25 um by MFI (#/mL) | 8 | 4 | 31 | 4 | 0 | 11 |
| ≥50 um by MFI (#/mL) | 0 | 0 | 8 | 0 | 0 | 4 |
| Total particles by MFI (#/mL) | 1284 | 4620 | 6848 | 5916 | 1047 | 4976 |
| Appearance | | | | | | |
| Concentration (mg/ml) | 58 | 64 | 66 | | | |
| pH | 6.197 | 6.184 | 6.184 | | | |
| Osmolality | 349 | 349 | 356 | | | |
| UV 280 (mg/ml) | | | | | | |
| SEC (% Initial) | 100 | | | 99.5 | 99.4 | 99.9 |
| IEX (% Initial) | 100 | | | 99.3 | 99.3 | 98.9 |
| CGE | 99.83 | | | 99.7 | 99.5 | |
| ELISA | 0.86 | | | 1.2 | 0.97 | 1.1 |

TABLE 32

Results (Part 2/3) of Pilot Stability Study
for 6% 1008, 9% sucrose, 20 mM citrate, 0.1% PS80 at pH 6.25

| Temp | 25° C. | | | | | |
|---|---|---|---|---|---|---|
| Time (wk) | 2 | 4 | 6.9 | 8 | 12 | 26 |
| ≥10 um by MFI (#/mL) | 46 | 50 | 206 | 27 | 38 | 157 |
| ≥25 um by MFI (#/mL) | 4 | 4 | 50 | 4 | 0 | 19 |
| ≥50 um by MFI (#/mL) | 0 | 0 | 11 | 0 | 0 | 0 |
| Total particles by MFI (#/mL) | 8186 | 6581 | 8679 | 2553 | 4143 | 10681 |
| Appearance | | | | | | |
| Concentration (mg/ml) | 66 | 75 | 69 | | | |
| pH | 6.209 | 6.198 | 6.196 | | | |
| Osmolality | 356 | 353 | 350 | | | |
| UV 280 (mg/ml) | | | | | | |
| SEC (% Initial) | 99.3 | 98.1 | 95.8 | 95.2 | 93.8 | 86.6 |
| IEX (% Initial) | 99.8 | 97.2 | 95.0 | 94.2 | 91.5 | 85.7 |
| CGE | 99.6 | 99.7 | | 99.6 | 99.3 | |
| ELISA | — | — | — | 1.1 | 0.92 | 1.1 |

TABLE 33

Results (Part 3/3) of Pilot Stability Study
for 6% 1008, 9% sucrose, 20 mM citrate, 0.1% PS80 at pH 6.25

| Temp | 40° C. | | | | | LC | FT |
|---|---|---|---|---|---|---|---|
| Time (week) | 0 | 1.1 | 2 | 4 | 6 | | 3 cycles |
| ≥10 um by MFI (#/mL) | 31 | 34 | 161 | 88 | 287 | | 138 |
| ≥25 um by MFI (#/mL) | 8 | 4 | 50 | 15 | 31 | | 19 |
| ≥50 um by MFI (#/mL) | 0 | 0 | 15 | 4 | 0 | | 0 |
| Total particles by MFI (#/mL) | 1284 | 3871 | 6306 | 29372 | 16081 | | 8415 |
| Appearance | | | | Cloudy, white precipitation observed | yellow | | |
| Concentration (mg/ml) | 58 | 66 | 65 | 74 | 57 | | 63 |
| pH | 6.20 | 6.18 | 6.22 | 6.24 | 6.16 | | 6.19 |
| Osmolality (mOsm/Kg) | 349 | 348 | 350 | 353 | 353 | | 349 |
| UV 280 (mg/ml) | | | | | | | |
| SEC (% Initial) | 100 | 95.6 | 88.6 | 72.9 | 10.5 | | 100 |
| IEX (% Initial) | 100 | 98.1 | 89.1 | 71.3 | n/a | | 100 |
| CGE | 99.8 | 99.8 | 99.0 | 98.6 | 34.9 | | 99.5 |
| ELISA | 0.86 | — | — | 0.87 | | | |

Exploratory Stability in Citrate Buffer: 60 mg/ml 1008 in 15 mm Citrate/6.75% Sucrose/0.05% PS80/pH 6.75

An exploratory stability in citrate buffer was conducted for the formulation of 60 mg/ml 1008 in 15 mM Citrate/6.75% Sucrose/0.05% PS80/pH6.75. The stability samples were stored at 5° C. and 25° C., as well as undergone freeze-thaw cycles. The samples were pulled according to the schedule shown in the table below, and analyzed for appearance, pH, osmolality, MFI, content, SEC, and IEX.

TABLE 34

Storage Condition and Pull Schedule for Interim Stability Studies

| Condition | Pull |
|---|---|
| 25° C. | 0, 1, 3, 6, and 9 months |
| 5° C. | 3, 6, and 9 months |
| Freeze Thaw (FT) | 3 cycles |

Similarly, exploratory stability in histidine buffer was conducted for formulation of 60 mg/ml 1008 in 15 mM histidine/6.75% Sucrose/0.05% PS80/pH6.75. The stability samples were stored at 5° C. and 25° C. The samples were also undergone freeze-thaw cycles. The samples were pulled according to the schedule shown in the table below, and analyzed for appearance, pH, osmolality, WI, content, SEC, and IEX.

TABLE 35

Storage Condition and Pull Schedule for Interim Stability Studies

| Condition | Pull |
|---|---|
| 25° C. | 0, 1, 3, and 6 months |
| 5° C. | 3 and 6 months |
| Freeze Thaw (FT) | 3 cycles |

The experimental data are tabulated in the tables below.

TABLE 36

Results (Part 1/2) of Interim Stability Study at 25° C.
60 mg/ml 1008 in 15 mM Citrate/6.75% Sucrose/0.05% PS80/pH 6.75

| Time (Month) | Initial | 1 | 3 | 6 | 9 |
|---|---|---|---|---|---|
| Particulates | | | | | |
| ≥10 um by MFI (#/mL) | 28 | 42 | 49 | 70 | |
| ≥25 um by MFI (#/mL) | 3 | 0 | 3 | 3 | |
| ≥50 um by MFI (#/mL) | 0 | 0 | 0 | 0 | |
| Total particles by MFI (#/mL) | 400 | 1819 | 2279 | 8355 | |
| ≥10 um by HIAC (#/mL) | 218.3 | | | | |
| ≥25 um by HIAC (#/mL) | 38.7 | | | | |
| ≥50 um by HIAC (#/mL) | 7.0 | | | | |
| Total particles by HIAC (#/mL) | 11170 | | | | |
| Appearance | | | | | |
| Color | Colorless | Colorless | Colorless | Colorless | |
| Clarity | NMT EP1 | NMT EP1 | NMT EP1 | NMT EP1 | |
| pH | 6.74 | 6.72 | 6.76 | | |
| Osmolality (mOsm) | 320 | | | | |
| SEC (% Initial) | 99.9 (% area) | 98.6 | 94.2 | 97.4 | |
| IEX (% Initial) | 97.0 (% area) | 98.4 | 94.2 | 91.0 | 89.9 |

TABLE 37

Results (Part 2/2) of Interim Stability Study 60 mg/ml 1008 in 15 mM Citrate/6.75% Sucrose/0.05% PS80/pH 6.75

| | Condition | | | |
|---|---|---|---|---|
| | 5° C. | | | Freeze-thaw |
| Time (Month) | 3 | 6 | 9 | 3 cycles |
| Particulates | | | | |
| ≥10 um by MFI (#/mL) | 56 | 63 | | 24 |
| ≥25 um by MFI (#/mL) | 14 | 6.95 | | 3 |
| ≥50 um by MFI (#/mL) | 0 | 0 | | 0 |
| Total particles by MFI (#/mL) | 1092 | 6322 | | 29052 |
| ≥10 um by HIAC (#/mL) | | | | 441 |
| ≥25 um by HIAC (#/mL) | | | | 67 |
| ≥50 um by HIAC (#/mL) | | | | 18 |
| Total particles by HIAC (#/mL) | | | | 27700 |
| Appearance | | | | |
| Color | Colorless | Colorless | | ND |
| Clarity | NMT EP1 | NMT EP1 | | ND |
| pH | 6.72 | — | | 6.71 |
| Osmolality (mOsm) | — | — | | 306 |
| SEC (% Initial) | 99.8 | 99.8 | | 99.7 |
| IEX (% Initial) | 100.0 | 99.4 | 99.9 | 99.5 |

TABLE 38

Results (Part 1/2) of Interim Stability Study at 25° C. 60 mg/ml 1008 in 15 mM Histidine/6.75% Sucrose/0.05% PS80/pH 6.75

| Time (Month) | Initial | 1 | 3 | 6 |
|---|---|---|---|---|
| Particulates | | | | |
| ≥10 um by MFI (#/mL) | 14 | 642 | 153 | 56 |
| ≥25 um by MFI (#/mL) | 3 | 54 | 14 | 3 |
| ≥50 um by MFI (#/mL) | 0 | 4 | 0 | 0 |
| Total particles by MFI (#/mL) | 302 | 20483 | 9805 | 13374 |
| ≥10 um by HIAC (#/mL) | 1493 | | | |
| ≥25 um by HIAC (#/mL) | 127 | | | |
| ≥50 um by HIAC (#/mL) | 15 | | | |
| Total particles by HIAC (#/mL) | 17341 | | | |
| Appearance | | | | |
| Color | Colorless | Colorless | Colorless | Colorless |
| Clarity | NMT EP1 | NMT EP1 | NMT EP1 | NMT EP1 |
| pH | 6.72 | | 6.70 | 6.70 |
| Osmolality (mOsm) | 286 | | | |
| SEC (% Initial) | 99.9 (% area) | 98.3 | 93.6 | 97.5 |
| IEX (% Initial) | 97.1 (% area) | 97.9 | 92.5 | 87.8 |

TABLE 39

Results (Part 2/2) of Interim Stability Study 60 mg/ml 1008 in 15 mM Histidine/6.75% Sucrose/0.05% PS80/pH 6.75

| | Condition | | |
|---|---|---|---|
| | 5° C. | | Freeze-thaw |
| Time (Month) | 3 | 6 | 3 cycles |
| Particulates | | | |
| ≥10 um by MFI (#/mL) | 167 | 59. | 17 |
| ≥25 um by MFI (#/mL) | 10 | 7 | 0 |
| ≥50 um by MFI (#/mL) | 3 | 0 | 0 |
| Total particles by MFI (#/mL) | 17404 | 7368 | 7607 |
| ≥10 um by HIAC (#/mL) | | | 756 |
| ≥25 um by HIAC (#/mL) | | | 175 |
| ≥50 um by HIAC (#/mL) | | | 51 |
| Total particles by HIAC (#/mL) | | | 27698 |
| Appearance | | | |
| Color | Colorless | Colorless | ND |
| Clarity | NMT EP1 | NMT EP1 | ND |
| pH | 6.70 | | 6.70 |
| Osmolality (mOsm) | — | — | 271 |
| SEC (% Initial) | 99.7 | 100.0 | 99.9 |
| IEX (% Initial) | 99.2 | 99.2 | 99.2 |

The experimental data indicated that the stability of the formulations tested were significantly enhanced, especially in suppressing the formation of particulate matters, comparing to that of the control formulation at a protein concentration of 60 mg/ml.

The stable solution formulation identified contained 15 mM Citrate/6.75% Sucrose/0.0505% PS80 as shown in Table 40.

TABLE 40

| Component | Concentration (W/V %) | Concentration Range (W/V %) |
|---|---|---|
| 1008 | 12 | 6-12 |
| Citric Acid, anhydrous | 0.009 | 0.006-0.012 |
| Trisodium citrate (dihydrate) | 0.428 | 0.285-0.57 |
| Sucrose | 6.75 | 6.75 |
| Polysorbate 80 | 0.05% | 0.05% |
| Hydrochloric acid or Sodium hydroxide | pH 6.75 | pH 6.75 |
| Water for injection | qs 100 | qs 100 |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

What is claimed is:

1. An aqueous pharmaceutical composition, comprising (i) 60 mg/ml to 120 mg/ml of an anti-VEGF antibody that comprises the sequences of SEQ ID NO: 1 and SEQ ID NO: 2, (ii) 4.5% to 9% (w/v) sucrose, (iii) a citrate buffer comprising 0.006% to 0.012% (w/v) citric acid and 0.2% to 0.6% trisodium citrate dihydrate (w/v), and (iv) 0.01% to 0.1% polysorbate 80, wherein the aqueous pharmaceutical composition is suitable for ophthalmic administration.

2. The aqueous pharmaceutical composition of claim 1, having a pH of 6.3 to 7.3.

3. The aqueous pharmaceutical composition of claim 2, wherein the pH of the composition is about 6.8.

4. The aqueous pharmaceutical composition of claim 1, wherein the antibody comprises the sequence of SEQ ID NO: 3.

5. The aqueous pharmaceutical composition of claim 1, wherein the concentration of the anti-VEGF antibody is about 60 mg/ml.

6. The aqueous pharmaceutical composition of claim 1, wherein the concentration of the anti-VEGF antibody is about 120 mg/ml.

7. A delivery device including the aqueous pharmaceutical composition of claim 1.

8. The delivery device of claim 7, which is a pre-filled syringe.

9. A pre-filled syringe comprising an aqueous pharmaceutical composition that comprises (i) 60 mg/ml to 120 mg/ml of an anti-VEGF antibody that comprises the sequences of SEQ ID NO: 1 and SEQ ID NO: 2, (ii) 4.5% to 9% (w/v) sucrose, (iii) a citrate buffer comprising 0.006% to 0.012% (w/v) citric acid and 0.2% to 0.6% trisodium citrate dihydrate (w/v), and (iv) 0.01% to 0.1% polysorbate 80, wherein the aqueous pharmaceutical composition is suitable for ophthalmic administration.

10. The pre-filled syringe of claim 9, wherein the aqueous pharmaceutical composition has a pH of 6.3 to 7.3.

11. The pre-filled syringe of claim 9, wherein the antibody comprises the sequence of SEQ ID NO: 3.

12. The pre-filled syringe of claim 9, wherein the concentration of the anti-VEGF antibody is about 60 mg/ml.

13. The pre-filled syringe of claim 9, wherein the concentration of the anti-VEGF antibody is about 120 mg/ml.

14. An aqueous pharmaceutical composition, comprising (i) about 60 mg/ml or about 120 mg/ml of an anti-VEGF antibody that comprises the sequences of SEQ ID NO: 1 and SEQ ID NO: 2, (ii) 4.5% to 9% (w/v) sucrose, (iii) a citrate buffer comprising 10 mM to 20 mM citrate, and (iv) 0.01% to 0.05% polysorbate 80, wherein the aqueous pharmaceutical composition is suitable for ophthalmic administration.

* * * * *

```
                              SEQUENCE LISTING

<160> NUMBER OF SEQ ID NOS: 10

<210> SEQ ID NO 1
<211> LENGTH: 120
<212> TYPE: PRT
<213> ORGANISM: Artificial Sequence
<220> FEATURE:
<223> OTHER INFORMATION: Synthetic heavy chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
        115                 120

<210> SEQ ID NO 2
<211> LENGTH: 111
<212> TYPE: PRT
<213> ORGANISM: Artificial Sequence
<220> FEATURE:
<223> OTHER INFORMATION: Synthetic light chain

<400> SEQUENCE: 2

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
            100                 105                 110

<210> SEQ ID NO 3
<211> LENGTH: 251
<212> TYPE: PRT
<213> ORGANISM: Artificial Sequence
<220> FEATURE:
```

<223> OTHER INFORMATION: Synthetic antibody construct

<400> SEQUENCE: 3

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Val Glu Ser Gly Gly Leu Val Gln
130                 135                 140

Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Pro Tyr Tyr Ala
            180                 185                 190

Thr Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250
```

<210> SEQ ID NO 4
<211> LENGTH: 252
<212> TYPE: PRT
<213> ORGANISM: Artificial Sequence
<220> FEATURE:
<223> OTHER INFORMATION: Synthetic antibody construct

<400> SEQUENCE: 4

```
Met Glu Ile Val Met Thr Gln Ser Pro Ser Thr Leu Ser Ala Ser Val
1               5                   10                  15

Gly Asp Arg Val Ile Ile Thr Cys Gln Ala Ser Glu Ile Ile His Ser
            20                  25                  30

Trp Leu Ala Trp Tyr Gln Gln Lys Pro Gly Lys Ala Pro Lys Leu Leu
        35                  40                  45

Ile Tyr Leu Ala Ser Thr Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Val Tyr Leu Ala Ser
                85                  90                  95
```

```
Thr Asn Gly Ala Asn Phe Gly Gln Gly Thr Lys Leu Thr Val Leu Gly
            100                 105                 110

Gly Gly Gly Gly Ser Gly Gly Gly Ser Gly Gly Gly Ser Gly
            115                 120                 125

Gly Gly Gly Ser Glu Val Gln Leu Val Glu Ser Gly Gly Leu Val
        130                 135                 140

Gln Pro Gly Gly Ser Leu Arg Leu Ser Cys Thr Ala Ser Gly Phe Ser
145                 150                 155                 160

Leu Thr Asp Tyr Tyr Tyr Met Thr Trp Val Arg Gln Ala Pro Gly Lys
                165                 170                 175

Gly Leu Glu Trp Val Gly Phe Ile Asp Pro Asp Asp Pro Tyr Tyr
            180                 185                 190

Ala Thr Trp Ala Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
        210                 215                 220

Val Tyr Tyr Cys Ala Gly Asp His Asn Ser Gly Trp Gly Leu Asp
225                 230                 235                 240

Ile Trp Gly Gln Gly Thr Leu Val Thr Val Ser Ser
                245                 250

<210> SEQ ID NO 5
<211> LENGTH: 11
<212> TYPE: PRT
<213> ORGANISM: Artificial Sequence
<220> FEATURE:
<223> OTHER INFORMATION: CDR H1

<400> SEQUENCE: 5

Gly Phe Ser Leu Thr Asp Tyr Tyr Tyr Met Thr
1               5                   10

<210> SEQ ID NO 6
<211> LENGTH: 16
<212> TYPE: PRT
<213> ORGANISM: Artificial Sequence
<220> FEATURE:
<223> OTHER INFORMATION: CDR H2

<400> SEQUENCE: 6

Phe Ile Asp Pro Asp Asp Pro Tyr Tyr Ala Thr Trp Ala Lys Gly
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: CDR H3

<400> SEQUENCE: 7

Gly Asp His Asn Ser Gly Trp Gly Leu Asp Ile
1               5                   10

<210> SEQ ID NO 8
<211> LENGTH: 11
<212> TYPE: PRT
<213> ORGANISM: Artificial Sequence
<220> FEATURE:
<223> OTHER INFORMATION: CDR L1

<400> SEQUENCE: 8
```

```
Gln Ala Ser Glu Ile Ile His Ser Trp Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: CDR L2

<400> SEQUENCE: 9

Leu Ala Ser Thr Leu Ala Ser
1               5

<210> SEQ ID NO 10
<211> LENGTH: 12
<212> TYPE: PRT
<213> ORGANISM: Artificial Sequence
<220> FEATURE:
<223> OTHER INFORMATION: CDR L3

<400> SEQUENCE: 10

Gln Asn Val Tyr Leu Ala Ser Thr Asn Gly Ala Asn
1               5                   10
```